(12) United States Patent
Mortarino et al.

(10) Patent No.: US 10,648,109 B2
(45) Date of Patent: May 12, 2020

(54) PLIABLE SILK MEDICAL DEVICE

(71) Applicant: Sofregen Medical Ireland Limited, Dublin (IE)

(72) Inventors: Enrico Mortarino, Hickory, NC (US); Jessica L. Akers, Cambridge, MA (US); Kantilal N. Patel, Goldsboro, NC (US)

(73) Assignee: Sofregen Medical Ireland Limited, Dublin (IE)

( * ) Notice: Subject to any disclaimer, the term of this patent is extended or adjusted under 35 U.S.C. 154(b) by 55 days.

(21) Appl. No.: 16/069,635

(22) PCT Filed: Jan. 26, 2017

(86) PCT No.: PCT/US2017/015175
§ 371 (c)(1),
(2) Date: Jul. 12, 2018

(87) PCT Pub. No.: WO2017/132405
PCT Pub. Date: Aug. 3, 2017

(65) Prior Publication Data
US 2019/0307917 A1    Oct. 10, 2019

Related U.S. Application Data

(60) Provisional application No. 62/289,021, filed on Jan. 29, 2016, provisional application No. 62/287,386, filed on Jan. 26, 2016.

(51) Int. Cl.
*D04B 21/12* (2006.01)
*A61F 2/00* (2006.01)
(Continued)

(52) U.S. Cl.
CPC ............ *D04B 21/12* (2013.01); *A61F 2/0059* (2013.01); *A61F 2/0063* (2013.01); *A61F 2/12* (2013.01);
(Continued)

(58) Field of Classification Search
CPC ........ D04B 21/06; D04B 21/08; D04B 21/10; D04B 21/12; A61F 2/0063; A61F 2/0068; A61F 2/12; A61F 2002/0068
See application file for complete search history.

(56) References Cited

U.S. PATENT DOCUMENTS 6,090,116 A * 7/2000 D'Aversa .............. A61F 2/0063
 57/243
6,287,316 B1 * 9/2001 Agarwal ............... A61F 2/0063
 606/151

(Continued)

*Primary Examiner* — Danny Worrell
(74) *Attorney, Agent, or Firm* — Wolf, Greenfield & Sacks, P.C.

(57) ABSTRACT

An implantable, pliable silk device (e.g., in a form of a knitted mesh) for use in human soft tissue support and/or repair that provides stretch or pliable properties, e.g., multi-directional elongation properties. Such a device permits physicians or users to alter or manipulate the device dimension and/or shape at the time of device implantation, thereby permitting the device to conform to the contour of a target area or tissue more easily and providing more precise positioning of the device over the target area or tissue. In some embodiments, the implantable pliable silk device comprises a knit pattern feature that substantially prevents unraveling and preserves the stability of the mesh when cut. For example, the pliable silk device is a knitted mesh comprising at least two yarns laid in a knit direction and engaging each other to define a plurality of nodes.

17 Claims, 3 Drawing Sheets

(51) Int. Cl.
  *A61F 2/12*   (2006.01)
  *A61L 31/04*  (2006.01)
  *A61L 31/00*  (2006.01)
  *D02G 3/02*   (2006.01)
  *D04B 21/08*  (2006.01)
  *D02G 3/28*   (2006.01)

(52) U.S. Cl.
  CPC ......... *A61L 31/005* (2013.01); *A61L 31/047* (2013.01); *D02G 3/02* (2013.01); *D04B 21/08* (2013.01); *A61F 2002/0068* (2013.01); *D02G 3/28* (2013.01); *D10B 2211/04* (2013.01); *D10B 2509/08* (2013.01)

(56) References Cited

U.S. PATENT DOCUMENTS

| | | | | |
|---|---|---|---|---|
| 6,638,284 B1* | 10/2003 | Rousseau | | A61F 2/0063 66/193 |
| 6,912,877 B2* | 7/2005 | Yokoyama | | D04B 21/06 66/195 |
| 6,946,003 B1* | 9/2005 | Wolowacz | | A61F 2/08 623/23.72 |
| 8,418,508 B2* | 4/2013 | Lecuivre | | A61F 2/0063 66/170 |
| 8,628,791 B2* | 1/2014 | Altman | | A61F 2/08 424/423 |
| 8,708,886 B2* | 4/2014 | Deegan | | D04B 21/16 66/169 A |
| 8,746,014 B2* | 6/2014 | Mortarino | | A61F 2/0063 66/170 |
| 2005/0228408 A1* | 10/2005 | Fricke | | A61F 2/0063 606/151 |
| 2011/0177151 A1* | 7/2011 | Knight | | A61L 27/3604 424/423 |
| 2011/0224703 A1* | 9/2011 | Mortarino | | A61F 2/0063 66/195 |
| 2011/0257665 A1* | 10/2011 | Mortarino | | A61F 2/0063 606/151 |
| 2011/0301717 A1* | 12/2011 | Becker | | A61L 17/06 623/23.72 |
| 2012/0150204 A1* | 6/2012 | Mortarino | | A61F 2/0063 606/151 |
| 2012/0184974 A1* | 7/2012 | Becker | | A61L 17/06 606/151 |
| 2013/0267137 A1* | 10/2013 | Peniston | | A61F 2/0063 66/203 |
| 2015/0148823 A1* | 5/2015 | Mortarino | | A61F 2/0063 66/17 |
| 2016/0228608 A1* | 8/2016 | Hakimi | | A61L 27/18 |
| 2018/0303592 A1* | 10/2018 | Taylor | | A61F 2/0063 |
| 2019/0062951 A1* | 2/2019 | Rizk | | D04C 1/02 |
| 2019/0307917 A1* | 10/2019 | Mortarino | | D04B 1/12 |

* cited by examiner

FIGURE 3

PLIABLE SILK MEDICAL DEVICE

CROSS-REFERENCE TO RELATED APPLICATIONS

This application is a national stage filing under 35 U.S.C. § 371 of International Application No. PCT/US2017/015175, filed Jan. 26, 2017, which claims the benefit under 35 U.S.C. § 119(e) of U.S. provisional application No. 62/287,386 filed Jan. 26, 2016 and U.S. provisional application No. 62/289,021 filed Jan. 29, 2016, the contents of each of which are incorporated by reference herein in their entirety.

TECHNICAL FIELD

Various aspects provided herein related to devices comprising silk fibroin mesh devices and methods of using the same for biomedical and cosmetic applications.

BACKGROUND

Certain existing meshes and scaffolds for soft tissue support are made of a synthetic polymer such as Teflon®, polypropylene, polyglycolic acid, polyester, or polyglactin 910. Biomaterials such a tissue based or tissue derived material, for example an acellular dermal matrix ("ADM") obtained from human and animal derived dermis have also been used but do not have the mechanical integrity of high load demand applications (e.g., ligaments, tendons, muscle, hernia repair) or the appropriate biological functionality because most biomaterials either degrade too rapidly (e.g., collagen, PLA, PGA, or related copolymers), or are non-degradable (e.g., polyesters, metal), and (in either case) lack functional autologous tissue ingrowth (e.g., important to assist transfer of a load bearing function from an implanted biomaterial as the biomaterial is bioresorbed by the body). In certain instances a biomaterial may misdirect tissue differentiation and development (e.g., spontaneous bone formation, granuloma formation, or tumor formation) because it lacks biocompatibility with surrounding cells and tissue. Additionally, a biomaterial that fails to degrade is typically associated with chronic inflammation and such a response is detrimental to (e.g., weakens) surrounding and adjacent tissue. Accordingly, there is a need to develop novel devices that are more effective for providing soft tissue support and/or promoting tissue ingrowth.

SUMMARY

Embodiments of some aspects described herein are based on, at least in part, discovery of new knitted silk fibroin meshes, for example, with capabilities to elongate in multiple directions, while still maintaining durability and strength, which permits users, e.g., physicians or surgeons, to manipulate or change their shape and/or dimension to conform to the contour of a target tissue or area (e.g., a three-dimensional tissue surface) without generating folds or pleatings in the knitted silk fibroin meshes during deployment or implantation of the knitted silk fibroin meshes, thereby promoting tissue ingrowth and providing support and/or repair to the target tissue or area.

Accordingly, various aspects described herein relate to a biodegradable (synonymously bioresorbable), biocompatible, pliable, knitted silk fibroin matrix, mesh or scaffold (the "device") and methods for making and using the device in surgical and cosmetic procedures where tissue support (e.g., soft tissue support) is desired. For example, the device can provide support to a soft tissue (e.g., a gland, organ, muscle, skin, ligament, tendon, cartilage, blood vessel or mesentery), e.g., through a load bearing function of the device, in various tissue reconstruction, augmentation, and/or repair procedures, including, e.g., breast reconstruction, breast augmentation, abdominal surgery, gastro-intestinal surgery, hernia repair, facial surgery such as face lift, and/or any body contouring procedures such as neck lift, arm lift, and/or buttock lift. The soft tissue support can be provided by the device itself (for example in conjunction with a hernia repair, or general soft tissue support) or by the device being used in conjunction with another implant, for example use of the device on or around a tissue expander or a breast implant used in a breast reconstruction or a breast augmentation surgical procedure. The device can also support in-growth of connective tissue and new soft tissue, and can be used for wound closure and/or general soft tissue support procedures.

The devices described herein may comprise a knitted network of silk fibroin yarns, wherein the knitted network is characterized in that elongation at break along a direction of the knitted network formation is greater than 85% or more and elongation at break along a width of the knitted network is greater than 85%, and that the average pore size of the knitted network is greater than 1 mm$^2$ or larger.

In some embodiments of the devices described herein, the knitted network exhibits one or more (e.g., 1, 2, 3, 4, 5, 6, 7, and/or 8) of the following characteristics:

(a) an average burst strength of about 0.3 MPa to about 1.5 MPa, or about 0.3 MPa to about 0.6 MPa; and/or (b) an average maximum tensile stress along the direction of the knitted network formation of about 0.2 MPa to about 0.4 MPa, or about 0.2 MPa to about 0.3 MPa; and/or (c) an average maximum tensile stress along the width of the knitted network of about 0.1 MPa to about 0.3 MPa, or about 0.15 MPa to about 0.2 MPa; and/or (d) an average tear strength along the direction of the knitted network formation of about 100 N to about 170 N or about 110 N to about 160 N; and/or (e) an average tear strength along the width of the knitted network of about 50 N to about 100 N or about 60 N to about 90 N; and/or (f) an average density of about 0.10 mg/mm$^3$ to about 0.15 mg/mm$^3$; and/or (g) an average elongation at a force of about 16 N along the direction of the knitted network formation of about 20% to about 50% or about 25% to about 40%; and/or (h) an average elongation at a force of about 16 N along the width of the knitted network formation of about 20% to about 60% or about 30% to about 50%.

The devices described herein have a unique knit pattern, which provides pliability (e.g., a characteristic in which there is a high percent elongation in multiple directions and/or ability to drape without creating folds in the devices) to permit more precise implantation and deployment over complex 3-dimensional tissue planes or surfaces. In addition, such a knit pattern allows for the devices to be manufactured on a large scale using industrial knitting machines.

In some embodiments of any of the devices described herein, the knitted network of silk fibroin yarns is formed by a process comprising at least one or more (e.g., one, two, three, or four) of the following steps: (i) knitting a first silk fibroin yarn in a first wale direction using a knit pattern 1/1-1/3-3/3-3/1 or a portion thereof; (ii) knitting a second silk fibroin yarn in a second wale direction using a knit pattern 3/1-1/1-1/3-3/3 or a portion thereof; (iii) knitting a third silk fibroin yarn in a first course direction using a knit pattern 1/1-5/5-5/5-3/3-3/3-5/5-5/5-3/3-3/3-7/7-7/7-3/3-3/3-5/5-5/5-3/3-3/3-5/5-5/5-3/3-3/3-5/5-5/5-3/3-3/3-5/5-5/5-3/3 or a portion thereof; and (iv) knitting a fourth silk fibroin yarn in a second course direction using a knit pattern 3/3-3/3-5/5-5/5-3/3-3/3-5/5-5/5-1/1-1/1-5/5-5/5-3/3-3/3-5/5-5/5-3/3-3/3-7/7-7/7-3/3-3/3-5/5-5/5-3/3-3/3-5/5-5/5 or a portion thereof. In some embodiments, the knitted network of silk fibroin yarns may be formed by a process comprising at least one or more (e.g., one, two, three, or four) of the following steps: (i) knitting a first silk fibroin yarn in a first wale direction using a knit pattern 3/1-1/1-1/3-3/3 or a portion thereof; (ii) knitting a second silk fibroin yarn in a second wale direction using a knit pattern 1/1-1/3-3/3-3/1 or a portion thereof; (iii) knitting a third silk fibroin yarn in a first course direction using a knit pattern 3/3-3/3-5/5-5/5-3/3-3/3-5/5-5/5-1/1-1/1-5/5-5/5-3/3-3/3-5/5-5/5-3/3-3/3-7/7-7/7-3/3-3/3-5/5-5/5-3/3-3/3-5/5-5/5 or a portion thereof; and (iv) knitting a fourth silk fibroin yarn in a second course direction using the knit pattern 1/1-5/5-5/5-3/3-3/3-5/5-5/5-3/3-3/3-7/7-7/7-3/3-3/3-5/5-5/5-3/3-3/3-5/5-5/5-3/3-3/3-5/5-5/5-3/3-3/3-5/5-5/5-3/3 or a portion thereof. Other patterns for the first, second, third, fourth silk fibroin yarns are possible.

The word "knit" is synonymous with the word "knitted", so that a knit silk fabric is the same as a knitted silk fabric. The device can be a warp knit or can be weft knit silk fabric. In one embodiment, the device is a pliable, biocompatible, warp knit, multi-filament silk fibroin fabric. A woven material or fabric is made by weaving, which is a process that does not use needles, and results in a fabric with different characteristics than a knit fabric. In particular, a woven fabric is made by a non-needle process using multiple yarns that interlace each other at right angles to form a structure wherein one set of yarn is parallel to the direction of fabric formation. Woven fabrics are classified as to weave or structure according to the manner in which warp and weft cross each other. The three main types of weaves (woven fabrics) are plain, twill, and satin. Woven (weaved) silk fabric, woven textiles and woven fabrics are not within the scope of the present invention. Non-woven fabrics are also not within the scope of the present invention. Non-woven (also refer to as bonded) fabrics are formed by having multiple fibers cohered together chemically or physically, without use of needles.

Unlike the excluded woven and non-woven materials, a knitted fabric is generally softer and more flexible because its thread is treated differently. Thus a knitted fabric is made by using needles (such as for example the needles of a single or double bed knit machine) to pull threads up through the preceding thread formed into a loop by the needle. Because a knitted fabric is made using needles the knitted fabric can have one or multiple yarns intermeshing (also referred as interloping). Preferably, the device is made of biodegradable silk and is a biocompatible, non-woven, knit, multi-filament silk fabric or mesh.

In some embodiments of any of the devices described herein, the device is a pliable, sterile surgical mesh or scaffold available in a variety of shapes and sizes for use in open surgical or in laparoscopic procedures. In some embodiments, a user (e.g., a physician or surgeon) can tailor or cut the device to a particular size and shape to suit the need of a certain application or procedure. The device is flexible and suited for delivery through a trocar, e.g., a laparoscopic trocar, due to its strength, tear resistance, suture retention, and ability to be cut in any direction without unraveling. The device can provide immediate physical and mechanical stabilization of a tissue defect through the strength and porous (scaffold-like) construction of the device. The device can be used as a transitory scaffold for soft tissue support and repair to reinforce deficiencies where weakness or voids exist that require the addition of material to obtain the desired surgical outcome.

In any embodiments of the devices described herein, the device can comprise multi-filament twisted silk fibroin yarns. The silk is made of silk fibroin fibers. In some embodiments of any of the devices described herein, silk fibroin yarns are made from sericin-extracted or sericin-depleted silk fibers, e.g., from *Bombyx mori* silkworm. Sericin, the glue-like protein coating the native silk fibroin, can be substantially removed by treating the raw silkworm fibers with dilute aqueous $Na_2CO_3$ and/or dilute aqueous soap. The sericin can be substantially removed either before or after the yarn is formed from individual silkworm fibers. In some instances, it may be desirable to substantially remove sericin after the knitted mesh device is made.

In some embodiments, the device is a pliable, knitted silk fibroin fabric intended for implantation in a human body. The devices have an open pore knit structure. Significantly, after implantation the device and ingrown native tissue can maintain at least about 70% (including, e.g., at least about 80%, at least about 90%, at least about 95%, at least about 98%, or more) of the time zero device strength (e.g., based on a mechanical property such as burst strength of the device measured prior to device implantation) at one month or at three months or at six months in vivo after the implantation. In some embodiments, after implantation the device can maintain at least at least about 70% (including, e.g., at least about 80%, at least about 90%, at least about 95%, at least about 98%, or more) of the time zero device weight (e.g., weight of the device measured prior to device implantation) at one month or at three months or at six months in vivo after the implantation. The device can be implanted without regard to orientation of the device and the combined thickness of the device following ingrowth of native tissue scaffold, which increases with time in vivo in the patient.

Some aspects described herein provide biocompatible surgical silk fibroin mesh devices for use in soft or hard tissue repair. Non-limiting examples of soft tissue repair include hernia repair, rotator cuff repair, pelvic floor repair, cosmetic surgery, breast augmentation surgery, implementation of a bladder sling, or the like. Non-limiting examples of hard tissue repair include bone repair, involve reconstructive plastic surgery, ortho trauma, or the like.

In some embodiments, the device described herein have an open or porous structure. Advantageously, the open or porous structure of the device allows tissue ingrowth as the silk fibroin forming the device is bioresorbed, at a rate that permits smooth transition of mechanical properties from the device to the new tissue. For example, the device can bioresorb at a rate that is sufficient to allow tissue in-growth while transferring the load-bearing responsibility to the native tissue. An embodiment of the device can be made from silkworm (e.g., *Bombyx mori*) silk fibroin or from spider silk. In some embodiments, the device can be made from silk fibroin yarns comprising silkworm fibers that retain their native protein structure and have not been dissolved and/or reconstituted. For example, the silkworm fibers can be obtained or derived from silk cocoons. In some embodiments, the silk fibroin yarns can be sericin-depleted.

In one embodiment, a process for making and/or obtaining a pliable, knitted silk fibroin mesh is provided. The process generally comprises: knitting a first silk fibroin yarn in a first wale direction using the knit pattern 1/1-1/3-3/3-

3/1; knitting a second silk fibroin yarn in a second wale direction using the knit pattern 3/1-1/1-1/3-3/3; knitting a third silk fibroin yarn in a first course direction using the knit pattern 1/1-5/5-5/5-3/3-3/3-5/5-5/5-3/3-3/3-7/7-7/7-3/3-3/3-5/5-5/5-3/3-3/3-5/5-5/5-3/3-3/3-5/5-5/5-3/3-3/3-5/5-5/5-3/3; and knitting a fourth silk fibroin yarn in a second course direction using the knit pattern 3/3-3/3-5/5-5/5-3/3-3/3-5/5-5/5-1/1-1/1-5/5-5/5-3/3-3/3-5/5-5/5-3/3-3/3-7/7-7/7-3/3-3/3-5/5-5/5-3/3-3/3-5/5-5/5, thereby obtaining a pliable knitted silk fibroin mesh.

In another embodiment, a process for making and/or obtaining a pliable, knitted silk fibroin mesh may comprise: knitting a first silk fibroin yarn in a first wale direction using the knit pattern 3/1-1/1-1/3-3/3; knitting a second silk fibroin yarn in a second wale direction using the knit pattern 1/1-1/3-3/3-3/1; knitting a third silk fibroin yarn in a first course direction using the knit pattern 3/3-3/3-5/5-5/5-3/3-3/3-5/5-5/5-1/1-1/1-5/5-5/5-3/3-3/3-5/5-5/5-3/3-3/3-7/7-7/7-3/3-3/3-5/5-5/5-3/3-3/3-5/5-5/5; and knitting a fourth silk fibroin yarn in a second course direction using the knit pattern 1/1-5/5-5/5-3/3-3/3-5/5-5/5-3/3-3/3-7/7-7/7-3/3-3/3-5/5-5/5-3/3-3/3-5/5-5/5-3/3-3/3-5/5-5/5-3/3, thereby obtaining a pliable knitted silk fibroin mesh.

In some embodiments of any process described herein, the two movements in the wale direction occur on separate needle beds, with alternate yarns. Loops formed on the course movements may be staggered within a repeat knit pattern.

In some embodiments of any of the devices or processes described herein, the silk fibroin yarns are made of sericin depleted silk fibers. In some embodiments, sericin is removed after the knitted mesh device is formed. In some embodiments, the silk fibroin yarns are nine filament, twisted yarns (e.g., a silk fibroin yarn includes nine silk fibroin filaments that are twisted to form a yarn, either at once or through twisting individual fiber bundles, such as three bundles of three yarns). For example, the yarns can be made with three ends of Td 20/22 raw silk twisted together in the S direction (clockwise direction of twist) to form a ply with 20 tpi and further combining 3 of the resulting ply with 10 tpi in the Z direction (counter clockwise direction of twist).

In some embodiments of any of the devices or processes described herein, the stitch density or pick count for the silk fibroin mesh can be between about 10 and about 100 picks per centimeter, for example, at least about 10, at least about 20, at least about 30, at least about 40, at least about 50, at least about 60, at least about 70, at least about 80, at least about 90 picks per centimeter; and/or less than or equal to 100, less than or equal to 90, less than or equal to 80, less than or equal to 70, less than or equal to 60, less than or equal to 50, less than or equal to 40, less than or equal to 30, less than or equal to 20 picks per centimeter. For example, about 10, about 20, about 30, about 40, about 50, about 60, about 70, about 80, or about 90 picks per centimeter. In one embodiment, the stitch density is about 40 picks per centimeter including the total picks count for the technical front face and the technical back face of the mesh, for example, about 20 picks per centimeter considering only one face of the mesh.

In any embodiment of the devices described herein, the pliable, knitted silk fibroin mesh can have an average elongation at break of between about 4%, or 32% to about 109% or 110%. In any embodiment of the devices described herein, the pliable, knitted silk fibroin mesh have an average elongation at break of about 85% to about 190%, or about 95% to about 150%. For example, in some embodiments, the elongation at break along a direction of the pliable silk fibroin mesh formation is greater than 85% or higher and the elongation at break along a width of the pliable silk fibroin mesh is greater than 85% or higher.

In any embodiment of the devices described herein, the pliable, knitted silk fibroin mesh can have a burst strength of about 0.3 MPa or higher. In one embodiment, the pliable, knitted silk fibroin mesh has a burst strength of about 0.45 MPa.

In another aspect, a pliable knitted silk fibroin mesh is provided, wherein the mesh is made or formed by a process comprising: knitting a first silk fibroin yarn in a first wale direction using the pattern 1/1-1/3-3/3-3/1; knitting a second silk fibroin yarn in a second wale direction using the pattern 3/1-1/1-1/3-3/3, knitting a third silk fibroin yarn in a first course direction using the pattern 1/1-5/5-5/5-3/3-3/3-5/5-5/5-3/3-3/3-7/7-7/7-3/3-3/3-5/5-5/5-3/3-3/3-5/5-5/5-3/3-3/3-5/5-5/5-3/3; and knitting a fourth silk fibroin yarn in a second course direction using the pattern 3/3-3/3-5/5-5/5-3/3-3/3-5/5-5/5-1/1-1/1-5/5-5/5-3/3-3/3-5/5-5/5-3/3-3/3-7/7-7/7-3/3-3/3-5/5-5/5-3/3-3/3-5/5-5/5.

In another aspect, a pliable knitted silk fibroin mesh is provided, wherein the mesh is made or formed by a process comprising: knitting a first silk fibroin yarn in a first wale direction using the knit pattern 3/1-1/1-1/3-3/3; knitting a second silk fibroin yarn in a second wale direction using the knit pattern 1/1-1/3-3/3-3/1; knitting a third silk fibroin yarn in a first course direction using the knit pattern 3/3-3/3-5/5-5/5-3/3-3/3-5/5-5/5-1/1-1/1-5/5-5/5-3/3-3/3-5/5-5/5-3/3-3/3-7/7-7/7-3/3-3/3-5/5-5/5-3/3-3/3-5/5-5/5; and knitting a fourth silk fibroin yarn in a second course direction using the knit pattern 1/1-5/5-5/5-3/3-3/3-5/5-5/5-3/3-3/3-7/7-7/7-3/3-3/3-5/5-5/5-3/3-3/3-5/5-5/5-3/3-3/3-5/5-5/5-3/3.

In some embodiments of the devices or processes described herein, the two movements in the wale direction occur on separate needle beds, for example, with alternate yarns and loops that occur on every course are staggered. In a specific embodiment, the silk fibroin yarns are made of a nine filament, twisted, and sericin depleted silk fibers. The yarns may be made with 3 ends of Td 20/22 raw silk twisted together in the S direction to form a ply with 20 tpi and further combining 3 of the resulting ply with 10 tpi in the Z direction. The stitch density or pick count for silk fibroin mesh design may be 40 picks per centimeter including the total picks count for the technical front face and the technical back face of the mesh, or equivalently 20 picks per cm considering only one face of the mesh.

In some embodiments of any of the devices described herein, the device is a pliable, knitted mesh having at least two silk fibroin yarns laid in a knit direction and engaging each other to define a plurality of nodes, the at least two yarns including a first yarn and a second yarn extending between and forming loops about two nodes, the second yarn having a higher tension at the two nodes than the first yarn, the second yarn substantially preventing the first yarn from moving at the two nodes and substantially preventing the knitted mesh from unraveling at the nodes. In some embodiments, the higher tension yarn is in a first wale direction and the lower tension yarn is in a second wale direction. In some embodiments, the higher tension yarn is in a first wale direction and the lower tension yarn is in a first course direction. In some embodiments, the higher tension yarn is in a first wale direction and the lower tension yarn is in a second course direction. In some embodiments, the higher tension yarn is in a second wale direction and the lower tension yarn is in a first wale direction. In some embodiments, the higher tension yarn is in a second wale direction and the lower tension yarn is in a first course direction. In some embodiments, the higher tension yarn is in a second wale direction and the lower tension yarn is in a second wale direction. In some embodiments, the higher tension yarn is in a first course direction and the lower tension yarn is in a first wale direction. In some embodiments, the higher tension yarn is in a first course direction and the lower tension yarn is in a second wale direction. In some embodiments, the higher tension yarn is in a first course direction and the lower tension yarn is in a second course direction. In some embodiments, the higher tension yarn is in a second course direction and the lower tension yarn is in a first wale direction. In some embodiments, the higher tension yarn is in a second course direction and the lower tension yarn is in a second wale direction. In some embodiments, the higher tension yarn is in a second course direction and the lower tension yarn is in a first course direction. In some embodiments, there is a difference in tension between two yarns that form inter-connecting loops. The device is a surgical mesh made of silk that is knitted, multi-filament, and bioengineered. It is mechanically strong, biocompatible, and long-term bioresorbable. The sericin-extracted silkworm fibroin fibers of the device retain their native protein structure and have not been dissolved and/or reconstituted.

Each and every feature described herein, and each and every combination of two or more of such features, is included within the scope of the present invention provided that the features included in such a combination are not mutually inconsistent.

The details of one or more embodiments of the disclosure are set forth in the description below. Other features or advantages of the present disclosure will be apparent from the following drawings and detailed description of several embodiments, and also from the appended claims.

BRIEF DESCRIPTION OF THE DRAWINGS

The present invention can be more fully understood from the detailed description and the accompanying drawings, which are not necessarily to scale, wherein:

Figure 3:
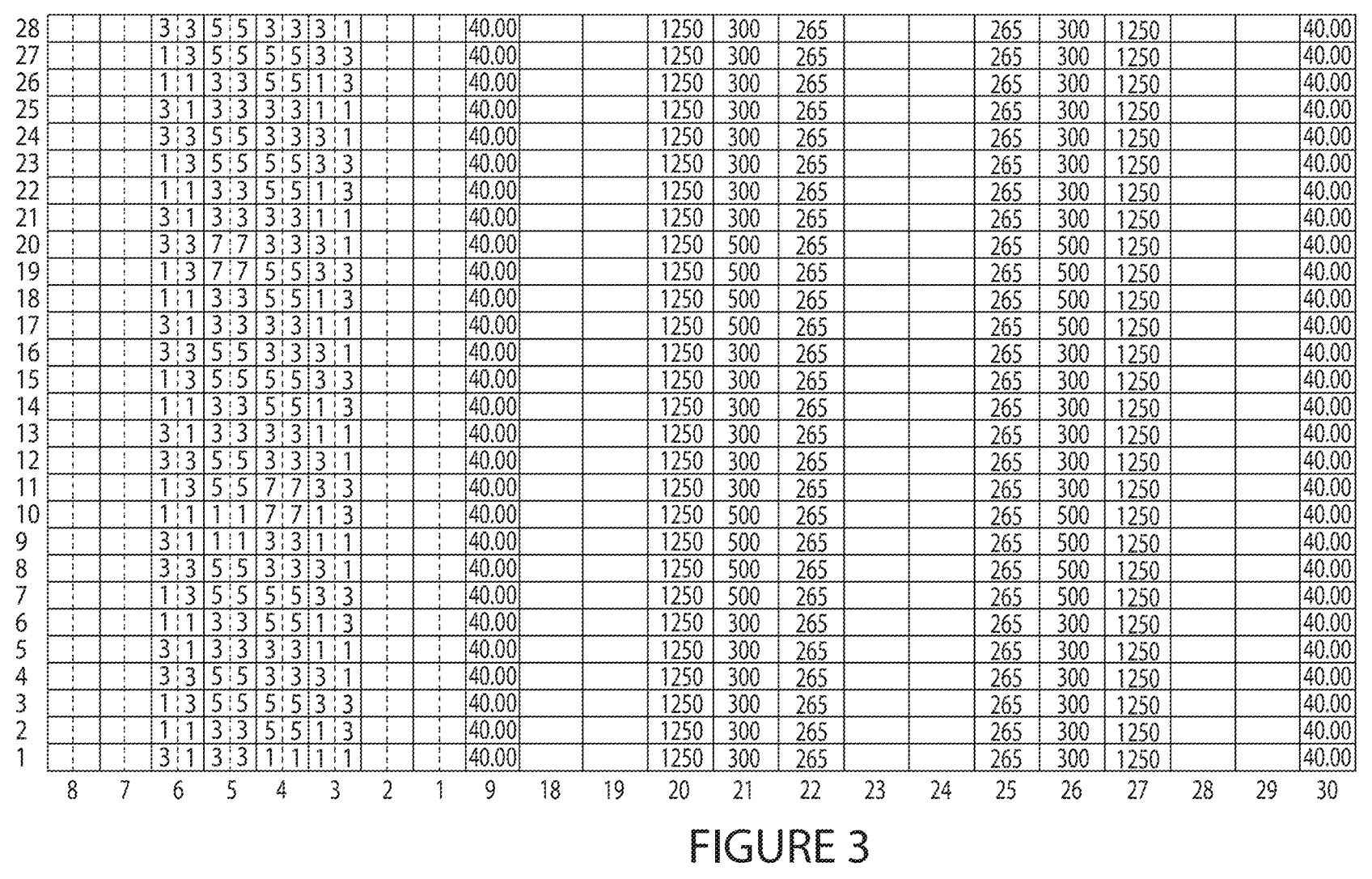

FIG. 3 shows exemplary feed rates for a knit pattern for making an embodiment of the devices described herein. Columns "1"-"8" are guide bars. The device can be made on four guide bars (3, 4, 5, 6), where guide bars 3 and 6 control the wale direction of the fabric (note the repeating pattern), while guide bars 3 and 5 control the course direction. Column "9" represents the speed (e.g., 40 stitches per inch or 40 courses per inch) at which a yarn is threading on a knitting machine. Column "30" represents the speed (e.g., 40 stitches per inch or 40 courses per inch) at which the knitted fabric is leaving the knitting machine. Columns "20"-"27" represent the speed and controls of the feed system. Rows "1"-"28" represent the number of courses.

DETAILED DESCRIPTION

Figure 1:
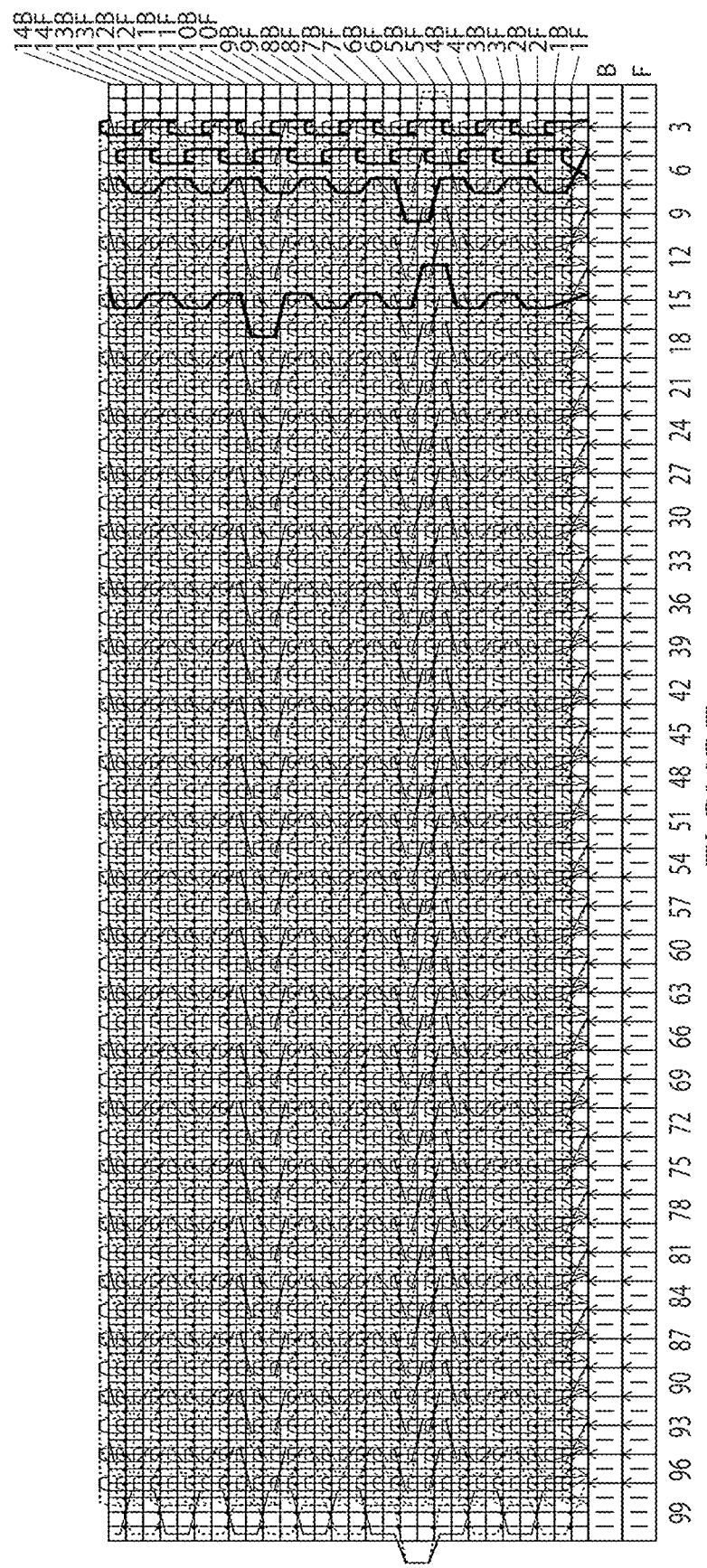
FIG. 1 represents a pattern layout for making an embodiment of the devices described herein on a raschel knitting machine. The figure shows the actual pattern which the needles take to move the thread through the knitting machine.
Figure 2:
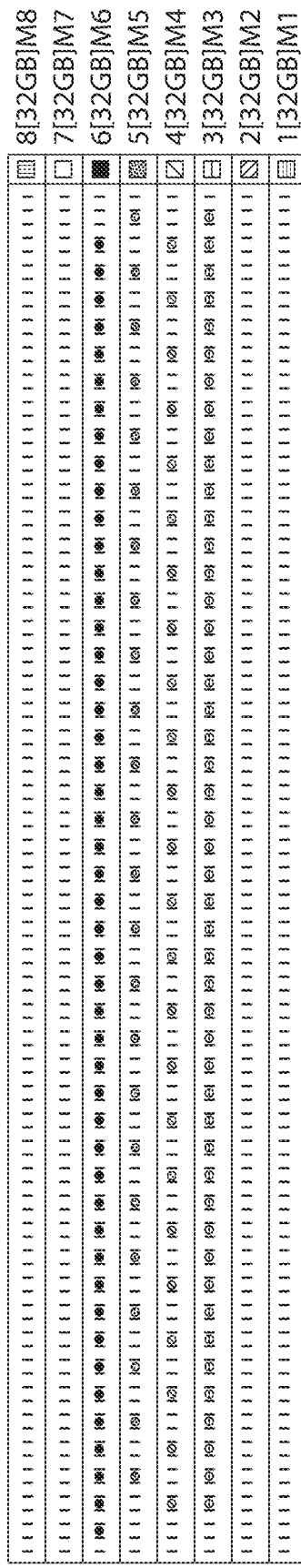
FIG. 2 represents a pattern layout for making an embodiment of the devices described herein on a raschel knitting machine. The figure shows the double needle bed pattern layout for making an embodiment of the device.

Embodiments of some aspects described herein are based on, at least in part, discovery of an implantable, bioresorbable, biocompatible, pliable, knitted, porous silk fibroin mesh (the "device") which upon implantation provides soft tissue support and tissue ingrowth and, as the device bioresorbs, transfer of its load bearing (support) function to new tissue formed at the site of implantation. The device is highly pliable, and smoothly drapeable, and can be used in surgery, for example, to support or augment tissue. In some embodiments, the device can be deployed with minimal pleating and bunching of the device, relative to certain existing surgical meshes that are stiffer and are more difficult to stretch in one or more directions (e.g., in two or more directions). For example, the unique knit pattern of the devices described herein provides multi-directional elongation capabilities which permits a user (e.g., a physician or surgeon) to be able to more precisely deploy the device, for example, into an irregular three-dimensional tissue pocket (or around implantable tissue augmentation devices, e.g., a breast implant), relative to stiffer surgical meshes. Thus, the devices described herein can be deployed in and around highly contoured tissue planes/surfaces or voids, e.g., where tissue has been removed or there has been significant tissue trauma. The devices described herein can be manipulated to conform to the contour of a tissue plane/surface or to fill a tissue void. For example, a device described herein can be stretched to conform to the contour of a tissue plane/surface. Alternatively, a device described herein can be compressed, folded, or rolled to form a three-dimensional pliable filler so as to fill a tissue void. The device can additionally or alternatively be stretched or pulled around another medical implant (e.g., a breast implant) to provide lift and secondary support. These advantageous properties are realized by various embodiments described herein, for example, embodiments of the devices comprising the specific knit patterns described in detail herein.

Silk is a natural (non-synthetic) protein made of high strength silk fibroin fibers with mechanical properties similar to or better than many of synthetic high performance fibers. Silk is also stable at physiological temperatures in a wide range of pH, and is insoluble in most aqueous and organic solvents. As a protein, unlike the case with most if not all synthetic polymers, the degradation products (e.g., peptides, amino acids) of silk are biocompatible. Silk is non-mammalian derived and carries far less bioburden than other comparable natural biomaterials (e.g. bovine or porcine derived collagen). Silk, as the term is generally known in the art, means a filamentous fiber product secreted by an organism such as a silkworm or spider. Silks can be made by certain insects such as for example *Bombyx mori* silkworms, and *Nephilia clavipes* spiders. There are many variants of natural silk. The silk fibroin is produced and secreted by a silkworm's two silk glands. As fibroin leaves the glands it is coated with sericin, a glue-like substance. Spider silks produced as a single filament lack the immunogenic protein sericin. Use of both silkworm silk and spider silk (from a natural source or made recombinantly) is within the scope of various aspects described herein.

In some embodiments of various aspects described herein, the device is made from silkworm silk, e.g., *Bombyx mori* silkworm silk. In some embodiments, it can be also made from spider silk, including recombinantly made spider silk. Silkworm silk has been used in biomedical applications. The *Bombyx mori* species of silkworm produces a silk fiber (a "bave") and uses the fiber to build its cocoon. The bave as produced include two silk fibroin filaments ("brins") which are surrounded with a coating of the gummy, antigenic protein sericin. Silk fibers harvested for making textiles, sutures and clothing are generally not sericin extracted or sericin depleted or, in some cases, are sericin depleted or only to a minor extent and typically retain at least 10% to 26% by weight sericin. Retaining the sericin component protects the frail silk fibroin filaments from fraying during textile manufacture. Hence textile grade silk generally includes sericin. Medical grade silkworm silk is used as either a virgin silk suture, where the sericin has not been removed, or as a silk fibroin suture from which the sericin has been substantially removed and may additionally include a wax or silicone coating to provide a barrier between the silk fibroin and the body tissue and cells. Physicians prefer and require an implantable, knitted silk fibroin medical device with the flexibility to be stretched, expanded, pulled into shape, elongated and/or draped into place over, around or under complex 3-dimensional soft tissue or implant at the time of a soft tissue surgical or medical procedure. Ideally, this silk fibroin medical device can be deployed without its elongation breaking, splitting or unraveling. Thus there is a need for such a pliable, sericin-extracted, implantable, bioresorbable silk fibroin medical device.

In some embodiments, the device described herein is made from silk fibroin fibers obtained from cocoons of silkworms, e.g., *Bombyx mori* silkworms. The raw silk fibers obtained from silkworms (e.g., *Bombyx mori* silkworms) comprise a fibroin protein core filament coated with the antigenic globular protein sericin. The sericin can be removed or substantially all removed by any methods known in the art, e.g., hot aqueous (e.g., soap) extraction (wash), $Na_2CO_3$, sericin-depletion methods described in the International Patent Publication No. WO2003043486, or a combination of any of these treatments, thus leaving behind silk fibroin protein filament essentially consisting of layers of antiparallel beta sheets which provide both stiffness and toughness. Accordingly, in some embodiments, the silk fibers in the devices described herein are sericin-depleted. As used herein, the term "sericin-depleted" refers to a device, a silk fiber, a silk filament, or a silk fibroin yarn that is substantially depleted of its native sericin content (e.g., about 5% (w/w) or less residual sericin in the final extracted silk). In some embodiments, the device, silk fiber, silk filament, or silk fibroin yarn has, e.g., about 0.1% (w/w) residual sericin (or more), about 1% (w/w) residual sericin (or more), about 2% (w/w) residual sericin (or more), about 3% (w/w) residual sericin (or more), about 4% (w/w) (or more), or about 5% (w/w) residual sericin (or more). In some embodiments, the device, silk fiber, silk filament, or silk fibroin yarn has, e.g., at most 1% (w/w) residual sericin, at most 2% (w/w) residual sericin, at most 3% (w/w) residual sericin, at most 4% (w/w), or at most 5% (w/w) residual sericin. Combinations of the above-referenced ranges are also possible. In some other embodiments, the device, silk fiber, silk filament, or silk fibroin yarn has, e.g., about 1% (w/w) to about 2% (w/w) residual sericin, about 1% (w/w) to about 3% (w/w) residual sericin, about 1% (w/w) to about 4% (w/w), or about 1% (w/w) to about 5% (w/w) residual sericin. In some embodiments, the device, silk fiber, silk filament, or silk fibroin yarn can be entirely free of its native sericin content. As used herein, the term "entirely free" means that within the detection range of the instrument or process being used, the substance cannot be detected or its presence cannot be confirmed. In some embodiments, the silk fibroin is essentially free of its native sericin content. As used herein, the term "essentially free" means that only trace amounts of the substance can be detected, is present in an amount that is below detection, or is absent.

As described above, the raw silk fibers have a natural globular protein coating known as sericin, which may have antigenic properties. Thus, in some embodiments, sericin can be depleted from the raw silk fibers before implantation. For example, the yarn can be taken through a depletion process as described, for example, by Gregory H. Altman et al., "Silk matrix for tissue engineered anterior cruciate ligaments," Biomaterials 23 (2002), pp. 4131-4141, the contents of which are incorporated herein by reference. As a result, the silk fibroin material used in the device embodiments contains substantially no (e.g., less than 5%) sericin. Alternatively, sericin can be removed from a silk filament or a silk fibroin yarn. For example, in some embodiments, a plurality of silk fibers (e.g., 3 or more sericin-containing silk fibers) are pulled together to form a "filament." Then a plurality of filaments (e.g., 3 or more filaments) are combined to make a multi-filament silk fibroin yarn (e.g., a 9-filament silk fibroin yarn). Sericin is removed and the silk fibroin yarns are threaded into knitting machines to form the devices described herein.

As used herein, "fibroin" includes silk fibroin from any sources, e.g., but not limited to silkworm silk fibroin (e.g., from *Bombyx mori*) and fibroin-like fibers obtained from insects or spiders (e.g., from *Nephilia clavipes*). Thus, any types of silk fibroin can be used according to various aspects described herein. Alternatively, silk protein suitable for use in the devices described herein can be obtained from a solution containing a genetically engineered silk, such as from bacteria, yeast, mammalian cells, transgenic animals or transgenic plants. See, for example, WO 97/08315 and U.S. Pat. No. 5,245,012.

In some embodiments, multiple sericin-depleted silk fibroin protein fibers are combined and twisted together to form a multi-filament yarn. The multi-filament silk fibroin yarn is subsequently knitted into a three-dimensional pattern to serve as soft tissue support and repair. The resulting device is mechanically strong, flexible, and tear-resistant. The device is a single use only scaffold that can be produced in a variety of shapes, sizes and thicknesses and can be terminally sterilized.

In some embodiments, the device has a knit pattern feature that substantially or entirely prevents unraveling, for example, when the device is cut. For example, the device has a stable knit pattern made by knitting silk fibroin yarn with variations of tension between at least two yarns laid in a knit direction. For example, a first yarn and a second yarn may be laid in a knit direction to form "nodes" for a mesh device. The knit direction for the at least two yarns, for example, may be vertical during warp knitting or horizontal during weft knitting. The nodes of a mesh device, also known as intermesh loops, refer to intersections in the mesh device where the two yarns form a loop around a knitting needle. In some embodiments, the first yarn is applied to include greater slack than the second yarn, so that, when a load is applied to the mesh device, the first yarn is under a lower tension than the second device. A load that places at least two yarns under tension may result, for example, when the mesh device is sutured or if there is pulling on the mesh device. The slack in the first yarn causes the first yarn to be effectively larger in diameter than the second yarn, so that the first yarn experiences greater frictional contact with the second yarn at a node and cannot move, or is "locked," relative to the second yarn. Accordingly, this particular knit design may be referred to as a "node-lock" design.

In one knit pattern for making the devices described herein, there is a variation in tension between yarns at the knit nodes (the yarn interlocking loops) thereby preventing unraveling of the mesh when cut for use in surgery. The variation in tension between yarns can be introduced by feeding the yarns at different rates.

To check the cutability of the devices described herein, the devices can be evaluated according to the number of scissor strokes needed to cut the device with surgical scissors. The mesh devices were found to be cut excellently because it took one to two scissor strokes to cut through it. The device was also cut diagonally and in circular patterns, indicating that the device did not unravel when cut in one or more of various directions, e.g., a device formation direction, a device width direction, and/or a diagonal direction. To determine further if the device would unravel, a suture can be passed through the closest pore from the cut edge, and pulled. This manipulation did not unravel the device. Thus the devices described herein are easy to cut and do not unravel after manipulation.

Advantageously, the devices described herein also allows significant and consistent tissue ingrowth while bioresorbing at a rate which permits smooth transfer of load bearing support to the newly formed tissue. Thus the device is made of a biocompatible silk protein that is eventually bioresorbed. "Bioresorbed" means that none or fewer than 10% (including, e.g., fewer than 9%, fewer than 8%, fewer than 7%, fewer than 6%, fewer than 5%, fewer than 4%, fewer than 3%, fewer than 2%, fewer than 1% or lower) of the silk fibroin fibers of the device can be seen to the naked (no magnification aid) eye upon visual inspection of the site of implantation of the device or of a biopsy specimen therefrom, and/or that the device is not palpable (e.g., cannot be felt by a surgeon at a time after the surgery during which the device was implanted) upon tactile manipulation of the dermal location of the patient at which the device was implanted. Typically either or both of these bioresorbed determinants occur about 1 to about 5 years after in vivo implantation of the device.

The devices described herein provide immediate physical and mechanical stabilization of tissue defects because of its strength and porous construction and is useful as a transitory scaffold for soft tissue support and repair. Further, the devices described herein can be more accurately deployed in and around complex 3-dimensional tissue planes and contours because of its pliable properties that extend from the yarn construction and knit pattern combination described herein. Thus, the devices described herein provide reinforcement for deficiencies where weakness or voids exist that require additional material reinforcement to obtain the desired surgical outcome. The bioresorption process occurs over time after implantation of the device as tissue in-growth and neovascularization takes place.

The devices described herein can be used to assist tissue repair, e.g., soft tissue repair. Examples of soft tissue repair include, but are not limited to, breast reconstruction, hernia repair, cosmetic surgery, implementation of a bladder sling, or the like.

A detailed explanation of a novel knit pattern and knit process used to make the device according to some embodiments described herein is set forth below.

The device may be formed on any double needle bed warp knitting machine. One such device is the raschel knitting machine, Comez DNB/EL-800-8B, set up in 10 gg needle spacing by the use of four movements: two movements in the wale direction, the vertical direction within the fabric, and two movements in the course direction, the horizontal direction of the fabric. In some embodiments, the movements in the wale direction occur on separate needle beds or on a double needle bed machine with alternate yarns and loops that occur on every course may be staggered within repeat.

In a particularly advantageous embodiment, the device described herein comprises a knit pattern such that a yarn follows a repeat pattern of 1/1-1/3-3/3-3/1 for one of the wale direction movements and 3/1-1/1-1/3-3/3 for the other wale direction movement. The interlacing of the loops within the fabric allows for one yarn to become under more tension than the other under stress, locking it around the less tensioned yarn, thereby keeping the fabric from unraveling when cut. The other movement in the course direction occurs in every few courses creating the porous design of the device. These yarns follow a pattern of 1/1-5/5-5/5-3/3-3/3-5/5-5/5-3/3-3/3-7/7-7/7-3/3-3/3-5/5-5/5-3/3-3/3-5/5-5/5-3/3-3/3-5/5-5/5-3/3-3/3-5/5-5/5-3/3 for the first course direction movement, and a pattern of 3/3-3/3-5/5-5/5-3/3-3/3-5/5-5/5-1/1-1/1-5/5-5/5-3/3-3/3-5/5-5/5-3/3-3/3-7/7-7/7-3/3-3/3-5/5-5/5-3/3-3/3-5/5-5/5 for the second course direction movement.

In another embodiment, the device described herein comprises a knit pattern such that a yarn follows a repeat pattern of 3/1-1/1-1/3-3/3 for one of the wale direction movements and 1/1-1/3-3/3-3/1 for the other wale direction movement. The interlacing of the loops within the fabric allows for one yarn to become under more tension than the other under stress, locking it around the less tensioned yarn, thereby keeping the fabric from unraveling when cut. The other movement in the course direction occurs in every few courses creating the porous design of the device. These yarns follow a pattern of 3/3-3/3-5/5-5/5-3/3-3/3-5/5-5/5-1/1-1/1-5/5-5/5-3/3-3/3-5/5-5/5-3/3-3/3-7/7-7/7-3/3-3/3-5/5-5/5-3/3-3/3-5/5-5/5 for the first course direction movement, and a pattern of 1/1-5/5-5/5-3/3-3/3-5/5-5/5-3/3-3/3-7/7-7/7-3/3-3/3-5/5-5/5-3/3-3/3-5/5-5/5-3/3-3/3-5/5-5/5-3/3-3/3-5/5-5/5-3/3 for the second course direction movement.

In some embodiments of any of the devices described herein, the knitted network of silk yarns is formed by a process comprising at least one or more (e.g., one, two, three, or four) of the following steps: (i) knitting a first silk yarn in a first wale direction using a knit pattern 1/1-1/3-3/3-3/1 or a portion thereof; (ii) knitting a second silk yarn in a second wale direction using a knit pattern 3/1-1/1-1/3-3/3 or a portion thereof; (iii) knitting a third silk yarn in a first course direction using a knit pattern 1/1-5/5-5/5-3/3-3/3-5/5-5/5-3/3-3/3-7/7-7/7-3/3-3/3-5/5-5/5-3/3-3/3-5/5-5/5-3/3-3/3-5/5-5/5-3/3-3/3-5/5-5/5-3/3 or a portion thereof; and (iv) knitting a fourth silk yarn in a second course direction using a knit pattern 3/3-3/3-5/5-5/5-3/3-3/3-5/5-5/5-1/1-1/1-5/5-5/5-3/3-3/3-5/5-5/5-3/3-3/3-7/7-7/7-3/3-3/3-5/5-5/5-3/3-3/3-5/5-5/5 or a portion thereof. In some embodiments, the knitted network of silk yarns may be formed by a process comprising at least one or more (e.g., one, two, three, or four) of the following steps: (i) knitting a first silk yarn in a first wale direction using a knit pattern 3/1-1/1-1/3-3/3 or a portion thereof; (ii) knitting a second silk yarn in a second wale direction using a knit pattern 1/1-1/3-3/3-3/1 or a portion thereof; (iii) knitting a third silk yarn in a first course direction using a knit pattern 3/3-3/3-5/5-5/5-3/3-3/3-5/5-5/ 5-1/1-1/1-5/5-5/5-3/3-3/3-5/5-5/5-3/3-3/3-7/7-7/7-3/3-3/3-5/5-5/5-3/3-3/3-5/5-5/5 or a portion thereof; and (iv) knitting a fourth silk yarn in a second course direction using the knit pattern 1/1-5/5-5/5-3/3-3/3-5/5-5/5-3/3-3/3-7/7-7/7-3/3-3/3-5/5-5/5-3/3-3/3-5/5-5/5-3/3-3/3-5/5-5/5-3/3 or a portion thereof. Other patterns for the first, second, third, fourth silk yarns are possible. For example, additional stitches can be added to either or both ends of the pattern for the first, second, third, and/or fourth silk yarns. Alternatively, a few stitches can be removed from either or both ends of the pattern for the first, second, third, and/or fourth silk yarns. Any modifications to the pattern for the first, second, third, and/or fourth silk yarns that do not significantly affect the pliability of the devices described herein are also within the scope as described herein.

The same yarn design may be used for the movements occurring in the wale and course directions. The yarn may be made with 3 ends of Td (denier count) 20/22 raw silk twisted together in the S direction (clockwise direction of twist) to form a ply with 20 tpi (turns per inch, which is the number of turns measured in an inch of yarn) and further combining three of the resulting ply with 10 tpi, e.g., in the Z direction (counter clockwise direction of twist).

In some embodiments, the stitch density or pick count for the silk fibroin mesh can be at least about 10, at least about 20, at least about 30, at least about 40, at least about 50, at least about 60, at least about 70, at least about 80, at least about 90, or at least about 100 picks per centimeter. In some embodiments, the stitch density or pick count for the silk fibroin mesh can be no more than 100, no more than 90, no more than 80, no more than 70, no more than 60, no more than 50, no more than 40, no more than 30, no more than 20, or no more than 10 picks per centimeter. Combinations of the above-referenced ranges are also possible. For example, in some embodiments, the stitch density or pick count for the silk fibroin mesh can be between about 10 and about 100 picks per centimeter, for example, about 10, about 20, about 30, about 40, about 50, about 60, about 70, about 80, about 90 picks per centimeter. In some embodiments, the stitch density or pick count for the silk fibroin mesh can be about 10 to about 60 picks per centimeter. In one embodiment, the stitch density is about 40 picks per centimeter. The stitch density described herein includes the total picks count for the technical front face and the technical back face of the mesh. For example, in one embodiment, the stitch density is about 40 picks per centimeter, including the total picks count for the technical front face and the technical back face of the mesh, for example, about 20 picks per centimeter considering only one face of the mesh. In one embodiment, the stitch density or pick count for the design is 34 picks per centimeter considering the total picks count for the technical front face and the technical back face of the fabric, or 17 picks per cm considering only on the face of the fabric.

The knit pattern of the invention can be knit to any width depending upon the knitting machine and can be knitted with any of the gauges available with the various crochet machines or warp knitting machines. Table 1 outlines the device fabric widths (e.g., as measured after the fabric is allowed to equilibrate or relax after completion of knitting) that may be achieved using different numbers of needle count on different gauge machines. The dimensions in Table 1 are approximate due to the shrink factor of the knitted fabric which depends on stitch design, stitch density, and yarn size used. One of ordinary skill in the art can change the knitting width, for example, by adjusting needle count. These parameters can also be adjusted to control consistency and quality of the final knitted mesh device in an industrial scale-up setting, where external factors (e.g., instrument alignment, etc.) may cause minor changes to the overall device being manufactured.

TABLE 1

| Gauge | Needle Count | | Knitting Width (mm) | |
|---|---|---|---|---|
| (stitches/inch) | From | To | From | To |
| 48 | 2 | 5656 | 0.53 | 2997.68 |
| 24 | 2 | 2826 | 1.06 | 2995.56 |
| 20 | 2 | 2358 | 1.27 | 2994.66 |
| 18 | 2 | 2123 | 1.41 | 2993.43 |
| 16 | 2 | 1882 | 1.59 | 2992.38 |
| 14 | 2 | 1653 | 1.81 | 2991.93 |
| 12 | 2 | 1411 | 2.12 | 2991.32 |
| 10 | 2 | 1177 | 2.54 | 2989.58 |
| 5 | 2 | 586 | 5.08 | 2976.88 |

In one embodiment, the device is knit with 9-filament, twisted silk fibroin yarns. A yarn was made from three silk bundles, each of which was comprised of individual silk fibrils. The 9-filament yarns were knit into the pliable device. The wales ran horizontally and the courses ran vertically along the device.

Physical properties of the devices described herein include thickness, density and pore sizes. Table 2 below shows physical characteristics of one embodiment of the devices described herein, as compared to certain existing meshes. The thickness of the device was measured utilizing a J100 Kafer Dial Thickness Gauge. A Mitutoyo Digimatic Caliper was used to find the length and width of the samples; and was used to calculate the density of the device. The density was found by multiplying the length, width and thickness of the mesh then dividing the resulting value by the mass. The pore size of the device was found by photographing the mesh with an Olympus SZX7 Dissection Microscope under 0.8× magnification. The measurements were taken using ImagePro 5.1 software and the values were averaged over several measurements, e.g., about 2 to about 30 measurements.

TABLE 2

| | Physical Characterization | | |
|---|---|---|---|
| Sample | Average Thickness (mm) | Average Pore Size (mm$^2$) | Average Density (g/cm$^3$) |
| Mersilene Mesh | 0.31 ± 0.01 | 0.506 ± 0.035 | 0.143 ± 0.003 |
| Bard Mesh | 0.72 ± 0.00 | 0.465 ± 0.029 | 0.130 ± 0.005 |
| Vicryl Knitted Mesh | 0.22 ± 0.01 | 0.064 ± 0.017 | 0.253 ± 0.014 |
| SERI ® Surgical Scaffold (e.g., knit on a single needle bed machine) | 1.00 ± 0.04 | 0.640 ± 0.409 | 0.176 ± 0.002 |
| One embodiment of the device described herein knit on a double needle bed machine | 0.89 ± 0.003 | 1.26 ± 0.400 | 0.13 ± 0.005 |

In one embodiment, a device for surgical use is provided which has a thickness between about 0.6 mm and about 1.2 mm. In some embodiments, the device may have a thickness of at least about 0.6 mm, at least about 0.7 mm, at least about 0.8 mm, at least about 0.9 mm, at least about 1 mm, at least about 1.1 mm, or at least about 1.2 mm. In some embodiments, the device has a thickness of no more than 1.5 mm, no more than 1.4 mm, no more than 1.3 mm, no more than 1.2 mm, no more than 1.1 mm, no more than 1.0 mm, no more than 0.9 mm, no more than 0.8 mm, no more than 0.7 mm, or no more than 0.6 mm. Combinations of the above-referenced ranges are also possible. For example, in some embodiments, the device may have a thickness of about 0.6 mm to about 1.5 mm, or about 0.6 mm to about 1.2 mm, or about 0.6 mm to about 1.0 mm.

The length and width of the devices described herein can vary to suit the need of different applications and/or size of a target tissue/area to be supported and/or repaired. In some embodiments, the device can be provided in dimensions that are larger than what is needed for a certain application where a user can tailor the device to an appropriate size (e.g., by cutting) to suit the need of a particular application. For example, in one embodiment, the device can have a width of about 10 cm and a length of about 25 cm. The width and length of the device can be controlled by needle count and gauge, e.g., as shown in Table 1 above. The widths and lengths are measured after the device is allowed to relax or equilibrate after completion of knitting.

In some embodiments, the device comprises pores with a size that allows for fluid egress and optimal tissue integration upon implantation. For example, the average area of a pore in the device is greater than about 1 mm$^2$, greater than about 1.5 mm$^2$, greater than about 2 mm$^2$, greater than about 2.5 mm$^2$, greater than about 3 mm$^2$, greater than about 3.5 mm$^2$, greater than about 4 mm$^2$, or greater than about 4.5 mm$^2$. In some embodiments, the average area of a pore in the device can be no more than about 5 mm$^2$, no more than about 4.5 mm$^2$, no more than about 4 mm$^2$, no more than about 3.5 mm$^2$, no more than about 3 mm$^2$, no more than about 2.5 mm$^2$, no more than about 2 mm$^2$, or no more than about 1.5 mm$^2$. Combinations of the above-referenced ranges are also possible. For example, the average area of a pore in the device can range from about 1 mm$^2$ to about 5 mm$^2$ or from about 2 mm$^2$ to about 4.5 mm$^2$, or from about 3 mm$^2$ to about 4.5 mm$^2$. The cross-sectional area of full pores of the device can be measured using a microscope with sufficient magnification and image capture capability. The magnification is selected based upon the resolution of the pores in the knit pattern being examined.

The density of the devices described herein can vary with the thickness of the silk fibroin yarn and/or pore size of the device. In some embodiments, the device can have a density of from about 0.1 mg/mm$^3$ to about 0.2 mg/mm$^3$ or from about 0.12 mg/mm$^3$ to about 0.18 mg/mm$^3$ or from about 0.12 mg/mm$^3$ to about 0.16 mg/mm$^3$. The density of the devices can be determined by dividing the mass of the device (e.g., dry mass) by its volume (e.g., [thickness, width, and length multiplied together]), wherein the volume is measured after the device is allowed to relax or equilibrate after completion of knitting. The density of the device is calculated using the equation:

$$\text{Material Density} = \frac{\text{Mass[mg]}}{(\text{Average Length[mm]}) \times (\text{Average Width[mm]}) \times (\text{Thickness[mm]})}$$

In some embodiments, the devices described herein may comprise at least about 95% silk fibroin, including, e.g., at least about 96%, at least about 97%, at least about 98%, at least about 99%, or up to 100% silk fibroin. Accordingly, in some embodiments, the devices described herein may comprise about 95%-100% silk fibroin.

In some embodiments, the devices described herein may exhibit a burst strength (or a maximum burst strength) of at least about 0.30 MPa, at least about 0.35 MPa, at least about 0.40 MPa, at least about 0.45 MPa, at least about 0.50 MPa, at least about 0.55 MPa, at least about 0.6 MPa, at least about 0.65 MPa, at least about 0.70 MPa, at least about 0.75 MPa, at least about 0.80 MPa, at least about 0.85 MPa, at least about 0.90 MPa, at least about 0.95 MPa, at least about 1.0 MPa, at least about 1.1 MPa, at least about 1.2 MPa, at least about 1.3 MPa, at least about 1.4 MPa, or at least about 1.5 MPa. In some embodiments, the devices described herein may exhibit a burst strength (or a maximum burst strength) of less than 2.0 MPa, less than 1.5 MPa, less than 1.4 MPa, less than 1.3 MPa, less than 1.2 MPa, less than 1.1 MPa, less than 1.0 MPa, less than 0.9 MPa, less than 0.8 MPa, less than 0.7 MPa, less than 0.6 MPa, less than 0.6 MPa, or less than 0.5 MPa. Combinations of the above-referenced ranges are also possible. For example, in some embodiments, the devices described herein can have a burst strength (or a maximum burst strength) of about 0.30 MPa to about 1.5 MPa, or about 0.4 MPa to about 0.8 MPa, or about 0.54 MPa to about 1.27 MPa. In one embodiment, the device described herein has a burst strength (or a maximum burst strength) of about 0.48 MPa.

The burst strength (or a maximum burst strength) of a device described herein can be determined by a ball burst testing per ASTM D3787-07. For example, each device tested can be compressed between two circular fixation brackets of the mechanical testing equipment, while leaving exposed a circular area of the test article that covers the radius of the inner fixture diameter. The sample device is secured with a constant fixation bolt torque to the locking nuts of the burst jig. Care is taken to ensure that the knit structure of the sample is organized and not skewed or sheared. The sample remains taut within the fixation brackets with equal distribution of tension (e.g., minimum tension). The ball burst fixture is attached to the mechanical testing equipment with a calibrated load cell. For the burst test, the fixture ball is inserted through the center diameter of the fixation brackets with a uniform pressure applied to the test article. The ball is inserted at a constant rate until the sample fails and thus the maximum burst load is recorded. In one embodiment, the ball is inserted at a rate of 2400 mm/min.

Maximum burst strength is calculated using the equation:

$$\text{Maximum Burst Strength}[MPa] = \left[\frac{\text{Maximum Burst Load}[N]}{\text{Exposed Area}[m^2]}\right] \times 10^{-6}$$

wherein the exposed area is the circular area of the test device covering the radius (r) of the inner fixture diameter and is calculated using the equation: Exposed Area=$\pi r^2$. In some embodiments, the maximum burst strength is determined using a sample size of about 4 cm in length and about 4 cm in width.

In some embodiments, the devices described herein are so pliable that they are able to drape as a fabric behaves. Drape is the ability of a fabric (e.g., a circular fabric of a known size) to deform when suspended under its own weight in specified conditions. The nature and extent of the deformation is dependent on the shear stiffness and bending stiffness of the fabric sample. Drape can be quantified using a drape coefficient as adapted from the British Standard (BS 5058: 1973) Method for the assessment of drape of fabrics. The drape coefficient is expressed as a ratio of a draped fabric area (e.g., fabric area viewable from the top) when it is partially supported underneath (Area$_{draped}$) to its undeformed flat state in terms of area (Area$_{flat}$) as shown in the equation:

$$\text{Drape Coefficient} = \text{Area}_{draped}/\text{Area}_{flat}$$

For example, the draft coefficient of a device described herein can be determined using a Micro-Vu Vertex 311HC with a 90-mm diameter circular sample. The Area$_{flat}$ is the area of the sample in its undeformed or flat state. To determine Area$_{draped}$, the circular sample is secured between two circular platens (a top and a bottom circular platen) each having a diameter that is 50% of the sample diameter such that the centers of the sample and platens are all aligned, resulting in a horizontal annular ring of fabric extending out from the platens. If the sample is pliable, the initially horizontally annular ring will drape around the bottom circular platen under gravity. Thus, the fabric area that is viewable above the top circular platen (Area$_{draped}$) would be smaller. In this case, the drape coefficient measures the deformation by gravity of an initially horizontal annular ring of fabric as it deforms with multi-directional curvature. In some embodiments, the devices described herein can display a drape coefficient of at least about 0.75, at least about 0.76, at least about 0.77, at least about 0.78, at least about 0.79, at least about 0.80, at least about 0.81, at least about 0.82, at least about 0.83, at least about 0.84, or at least about 0.85. In some embodiments, the devices described herein may display a drape coefficient of no more than about 0.97, no more than about 0.95, no more than about 0.85, no more than about 0.84, no more than about 0.83, no more than about 0.82, no more than about 0.81, or no more than about 0.80. Combinations of the above-referenced ranges are also possible. For example, in some embodiments, the devices described herein may display a drape coefficient of about 0.80 to about 0.90 or about 0.80 to about 0.85. In one embodiment, the device described herein display a drape coefficient of about 0.83. The smaller the drape coefficient is, the more flexible (e.g., more easily to be bent) a sample is.

In one embodiment, a device for surgical use is provided which has a thickness between about 0.6 mm and about 1.20 mm, a width of about 10 cm (±about 1 cm) and a length of about 25 cm (±about 3 cm). Additionally the device has pores with an average diameter greater than about 10,000 um$^2$, a density of from about 0.14 mg/mm$^3$ to about 0.18 mg/mm$^3$, and is comprised of at least about 95% silk fibroin. Furthermore, the device has a burst strength of from about 0.48 MPa to about 1.27 MPa, and a drape coefficient of between 0.75 to 0.97, e.g., 0.83.

In some embodiments of any devices described herein, the device can be characterized in that an average elongation at break along a "device formation direction" is at least about 85% or more including, e.g., at least about 90%, at least about 95%, at least about 100%, at least about 110%, at least about 120%, at least about 130%, at least about 140%, at least about 150%, at least about 160%, at least about 170%, at least about 180%, at least about 190%, or higher. In some embodiments, the average elongation along the device formation direction may be no more than about 195%, no more than about 190%, no more than about 180%, no more than about 170%, no more than about 160%, no more than about 150%, no more than about 140%, no more than about 130%, no more than about 120%, no more than about 110%, no more than about 100%, or lower. Combinations of the above-referenced ranges are also possible. For example, in some embodiments, the average elongation at break along a device formation direction is about 100% to about 190%, about 110% to about 150%, or about 100% to about 140%. As used herein, the term "device formation direction" refers to a direction that a silk fibroin mesh is formed and leaves a knitting machine.

In some embodiments of any devices described herein (e.g., devices that exhibit average elongation at break along a device formation direction of any of the above-referenced ranges), the device can be characterized in that an average elongation at break along a "device width direction" is at least about 85% or more including, e.g., at least about 90%, at least about 95%, at least about 100%, at least about 110%, at least about 120%, at least about 130%, at least about 140%, at least about 150%, at least about 160%, at least about 170%, at least about 180%, at least about 190%, or higher. In some embodiments, the average elongation along the device width direction may be no more than about 195%, no more than about 190%, no more than about 180%, no more than about 170%, no more than about 160%, no more than about 150%, no more than about 140%, no more than about 130%, no more than about 120%, no more than about 110%, no more than about 100%, or lower. Combinations of the above-referenced ranges are also possible. For example, in some embodiments, the average elongation at break along a device width direction is about 90% to about 190%, or about 95% to about 130%, or about 90% to about 120%. As used herein, the term "device width direction" refers to a direction that is perpendicular to the direction that a silk fibroin mesh is formed and leaves a knitting machine. That is, the device width direction is perpendicular to the device formation direction.

The average elongation at break along a device formation direction or a device width direction can be performed with a tensile testing in accordance with ASTM D5035, for example, using a sample size of about 60 mm in length and about 40 mm in width. It should be noted that a sample is cut from a silk fibroin mesh according to whether the device formation direction or the device width direction is evaluated. For example, a sample is cut lengthwise along the device formation direction (or mesh formation direction) for measurements of the average elongation at break along the device formation direction. Similarly, a sample is cut lengthwise along the device width direction (or mesh width direction) for measurements of the average elongation at break along the device width direction. The samples are incubated in phosphate buffered saline at 37° C. for about 2 hours before the testing.

In accordance with ASTM D5035, device samples are clamped in a mechanical test equipment. The upper clamp is mounted to a load cell, which is attached to the actuator and the lower clamp is mounted to a support plate. The lower limit of the actuator is set so that the upper and lower clamps are prevented from colliding. The upper clamp is aligned to make the faces of both clamps parallel to each other. The height of the mechanical equipment crosshead is adjusted so that the actuator is positioned to allow for a defined amount of upward movement and a specific sample gauge length resided between the upper and lower sample clamps.

For example, a sample (e.g., with a size of about 60 mm in length and about 40 mm in width) is loaded by clamping the first 10 mm of the sample into the upper clamp and allowing the remainder of the sample to fall unrestrained into the bottom clamp opening. The last 10 mm of the sample is held by the bottom clamp. Care is taken to avoid pre-straining the device sample. Once the sample is clamped the actuator height is adjusted so that the sample had a pre-load of about 0-2 N. The actuator position is adjusted to achieve a specific gauge length (e.g., 40 mm) and then reset to the zero-position at this point. The device sample is strained at an appropriate rate (e.g., about 1920 N/min) until it experiences ultimate tensile failure. The percent elongation at break is then determined using the following equation:

$$PercentElongationBreak[\%] = \left[\frac{\text{Elongation at Break[mm]}}{\text{Length[mm]}}\right]\%$$

wherein length is provided by the respective device sample length measurement.

Some embodiments of the devices described herein can be knitted on a fine gauge crochet knitting machine. A non-limiting list of crochet machines capable of manufacturing the silk fibroin meshes described herein are provided by: Changde Textile Machinery Co., Ltd.; Comez; China Textile Machinery Co., Ltd.; Huibang Machine; Jakkob Muller AG; Jingwei Textile Machinery Co., Ltd.; Zhejiang Jingyi Textile Machinery Co., Ltd.; Dongguan Kyang the Delicate Machine Co., Ltd.; Karl Mayer; Sanfang Machine; Sino Techfull; Suzhou Huilong Textile Machinary Co., Ltd.; Taiwan Giu Chun Ind. Co., Ltd.; Zhangjiagang Victor Textile; Liba; Lucas; Muller Frick; and Texma.

Some embodiments of the devices described herein can be knitted on a fine gauge double needle bed warp knitting machine. A non-limiting list of warp knitting machines capable of manufacturing the silk fibroin meshes described herein are provided by: Comez; Diba; Jingwei Textile Machinery; Liba; Lucas; Karl Mayer; Muller Frick; Runyuan Warp Knitting; Taiwan Giu Chun Ind.; Fujian Xingang Textile Machinery; and Yuejian Group.

Some embodiments of the devices described herein can be knitted on a fine gauge flat bed knitting machine. A non-limiting list of flat bed machines capable of manufacturing the silk fibroin meshes are provided by: Around Star; Boosan; Cixing Textile Machine; Fengshen; Flying Tiger Machinary; Fujian Hongqi; G & P; Gorteks; Jinlong; JP; Jy Leh; Kauo Heng Co., Ltd.; Matsuya; Nan Sing Machinery Limited; Nantong Sansi Instrument; Shima Seiki; Nantong Tianyuan; and Ningbo Yuren Knitting.

In some embodiments of the devices described herein, the device can bioresorb by at least about 50% (including, e.g., at least about 60%, at least about 70%, at least about 80%, at least about 90%, or more) in approximately 100 days after implantation of the device in a patient (e.g., a human patient). In some embodiments, the device can bioresorb by no more than about 90% (including, e.g., no more than about 80%, no more than about 70%, no more than about 60%, no more than about 50%, or lower) in approximately 100 days after implantation of the device in a patient (e.g., a human patient). Combinations of the above-referenced ranges are also possible. For example, the device can bioresorb by about 50% to about 90% in approximately 100 days after implantation of the device in a patient (e.g., a human patient). The bioresorption can be measured by change in the mass of the device after implantation. For example, at least about 50% (including, e.g., at least about 60%, at least about 70%, at least about 80%, at least about 90%, or more) of the mass of the device bioresorbs in about 100 days after implantation in a patient (e.g., a human patient). In some embodiments, no more than about 90% (including, e.g., no more than about 80%, no more than about 70%, no more than about 60%, no more than about 50%, or lower) of the mass of the device bioresorbs in 100 days after implantation of the device in a patient (e.g., a human patient). Combinations of the above-referenced ranges are also possible. For example, about 50% to about 90% of the mass of the device may bioresorb in about 100 days after implantation of the device in a patient (e.g., a human patient).

EXAMPLES

Example 1: Pliable Silk Medical Device

A pliable silk medical device ("the device" in Examples 1-6) and methods for making the device was developed. By pliable it is meant herein that the device can stretched to increase its length and/or its width by between about 90% and about 195% before breaking or between about 90% and about 140% before breaking (e.g., see % elongation at break—FF/FW shown in Tables 4-5 below). Unlike the silk medical devices described in the U.S. Patent Application Publication Nos. US 2015/0148823 and US 2016/0193026, and International Patent Publication No. WO2016/028797), the devices described herein comprise a unique knitting pattern that provides improved pliability without generating folds or pleating in the mesh (see Table 4), and thus promotes tissue ingrowth. Typically, generation of folds or pleats during implantation can increase the apparent thickness of a device and this would adversely affect tissue ingrowth. The unique knitting pattern also allows the device to be made on a double needle bed industrial knitting machine, at speeds appropriate for commercial scale-up and manufacturing. Additionally, the devices described herein differ from other silk medical devices such as SERI® Surgical Scaffold (e.g., as described in Horan et al.; "Biological and biomechanical assessment of a long-term bioresorbable silk-derived surgical mesh in an abdominal body wall defect model," Hernia 13 (2009) pp. 189-199) in all physical parameters including pliability, thickness, pore size, density and drapability. The device is a pliable, knitted, biocompatible silk fibroin scaffold device that can be implanted in a surgical procedure to provide soft tissue repair and soft tissue support, including supporting an implant such as a breast implant or a tissue expander or for reinforcing areas of the body where there has been a loss of soft tissue due to injury or disease. Examples of soft tissue repair surgical procedures include but are not limited to hernia repair, rotator cuff repair, pelvic floor repair, cosmetic surgery, breast augmentation surgery, implementation of a bladder sling, or the like. Although the device can employ a variety of polymer materials, preferable the device is made of silk, such as *Bombyx mori* silkworm silk fibroin. The raw silk fibers used to make the device have a natural globular protein coating known as sericin, which may have antigenic properties and must be depleted before implantation of the device. Accordingly, yarn used to make the device is taken through a sericin depletion process as described in Altman et al., "Silk matrix for tissue engineered anterior cruciate ligaments," Biomaterials 23 (2002), pp. 4131-4141, the contents of which are incorporated herein by reference in its entirety. After the depletion process the silk fibroin material used in the device embodiments contains substantially no sensitizing agents.

The device is preferably made by knitting sericin depleted silk fibroin yarn to form a porous mesh or fabric. The knitting can be carried out as raschel knitting, warp knitting and weft knitting. After being knitted, the fabric of the device can be treated to enhance one or more device characteristics. The device treatment can be a finishing or surface coating process which can increase device hydrophilicity, biocompatibility and mechanical properties, such as handling for ease of cutting and graft pull-through, as well as adding anti-microbial or anti-fungal coatings. Examples of device surface treatments can include, but are not limited to:

plasma modification protein such as but not limited to fibronectin, denatured collagen or gelatin, collagen gels and hydrophobic by covalent link or other chemical or physical method peptides with hydrophilic and a hydrophobic end peptides contain one silk-binding sequence and one biologically active\ sequence biodegradable cellulose surface sulfonation ozone gas treatment physically bound and chemically stabilized peptides DNA/RNA aptamers Peptide Nucleic Acids Avimers modified and unmodified polysaccharide coatings carbohydrate coating anti-microbial coatings anti-fungal coatings phosphorylcholine coatings As shown in Table 1 above, devices of varying width were made using different numbers of needles (needle count) on different gauge knitting machines. The device can be knit to any width limited by the knitting machine width and could be knitted with any of the gauges available with the various warp knitting machine.

Some embodiments of the devices described herein can be knitted on a fine gauge warp knitting machine. The following is an exemplary list of warp knitting machines capable of manufacturing the device: Comez; Diba; Jingwei Textile Machinery; Liba; Lucas; Karl Mayer; Muller Frick; Runyuan Warp Knitting; Taiwan Giu Chun Ind.; Fujian Xingang Textile Machinery; and Yuejian Group.

Some embodiments of the device were knitted on a COMEZ DNB/EL-800-8B/P—20 warp knitting machine in 20 gauge with stroke for each of the positions from 1 through 30 as shown in Table 3.

TABLE 3

| Position | Maximum stroke (mm) per pattern line |
|---|---|
| 1-8 | 1.25-60.00 |
| 9 | 0.33-1.00 |
| 11-29 | 0.01-38.65 |
| 30 | 0.33-1.00 |

The device, in some embodiments, has deformation properties that can be controlled by varying parameters within the device design, as set forth below to achieve desired device deformation (e.g., pliable) properties. A preferred and desired deformation property is the ability of the knitted device to exhibit at least about a 90-135% extension of its length in the machine direction and at least about 90-120% extension of its length in the cross direction without breaking or unraveling. These device properties are desired because they provide stretch or pliability for the physician user at the time of device implantation, therefor permitting the user to alter the device dimensions and/or shape at the time of device implantation to conform to the contour of a tissue plane or void.

In some embodiments, the movements in the wale direction occur on separate needle beds with alternate yarns; loops that occur on every course are staggered within repeat. While being knit the yarn follows a repeat pattern of 3/1-1/1-1/3-3/3 for one of the wale direction movements and 1/1-1/3-3/3-3/1 for the other wale direction movement, with each number representing a position, each "/" representing a guide bar movement, and each "-" representing a course (or stitch). For example, a yarn following a pattern of 3/1-1/1-1/3-3/3 would start in position 3 (located between the second and third needle slots) and move, as indicated by the "/", to position 1. The knitting needles would form a stitch (as indicated by the "-"), remain in position 1 (since 1/1 represents no movement), form another stitch, move from position 1 to position 3, form another stitch, and then remain in position 3 (since 3/3 would also represent no movement). The pattern would repeat for the full length of the fabric. The same notation method can be applied to all stitch patterns and on all guide bars listed.

The interlacing of the loops within the fabric of the device as it is being knit allow for one yarn to be under more tension than the other under stress, locking it around the less tensioned yarn; keeping the fabric from unraveling when cut. One of the other two movements in the course direction occurs in every few courses creating the porous design of the scaffold. As being knit these yarns follow a repeat pattern of 1/1-5/5-5/5-3/3-3/3-5/5-5/5-3/3-3/3-7/7-7/7-3/3-3/3-5/5-5/ 5-3/3-3/3-5/5-5/5-3/3-3/3-5/5-5/5-3/3-3/3-5/5-5/5-3/3 for the course direction movement. The other movements in the course direction occur in every few courses creating the openings in the scaffold. These yarns follow a repeat pattern of 3/3-3/3-5/5-5/5-3/3-3/3-5/5-5/5-1/1-1/1-5/5-5/5-3/3-3/3-5/5-5/5-3/3-3/3-7/7-7/7-3/3-3/3-5/5-5/5-3/3-3/3-5/5-5/5 for the course direction movement. The pattern adopts a yarn design made with 3 ends of Td 20/22 raw silk twisted together in the S direction to form a ply with 20 tpi and further combining 3 of the resulting ply with 10 tpi in the Z direction. The same yarn design is used for the movements occurring in the wale and course directions. The stitch density or pick count for the scaffold design is preferably 40 picks per centimeter including the total picks count for the technical front face and the technical back face of the fabric, or equivalently 20 picks per cm considering only one face of the fabric. The operating parameters are not limited to those described but just the optimum values for the physical properties of the device as a mesh or scaffold with the knit structure set forth which includes a twisted yarn. Sericin is preferably removed from the silk fibroin fibers after the yarn is formed (that is after the silk fibroin fibers have been twisted together, but not yet knitted) but before the mesh has been knit and/or after the device has been knitted. A preferred embodiment of the device is made of a 9 filament, twisted, and purified (sericin depleted) silk fibroin fiber. Once so formed into yarn (made from the twisted silk fibroin fibers) the yarn is then warp knitted as set forth above to thereby make the device. The properties of one mesh device in accordance with the present exemplary embodiment include improved drapeability, stretch, and conformability as compared to prior art silk fibroin mesh, as shown in Table 4 below.

TABLE 4

| Test Parameter | SERI ® Surgical Scaffold | Silk fibroin mesh device described in US App. Pat. Pub. No. US 2015/0148823 | One embodiment of the devices described herein |
|---|---|---|---|
| % Elongation at break-FF | 51[1] | 109[2] | 112[2] |
| % Elongation at break-FW | 33[1] | 81.36[2] | 103[2] |

TABLE 4-continued

| Test Parameter | SERI® Surgical Scaffold | Silk fibroin mesh device described in US App. Pat. Pub. No. US 2015/0148823 | One embodiment of the devices described herein |
|---|---|---|---|
| % Elongation at 16 N-FF | 6.8[1] | 33.3[2] | 31[2] |
| % Elongation at 16 N-FW | 3.9[2] | 32.1[2] | 39[2] |

[1]n = 4 devices average
[2]n = 20 devices average
Table Legend
FF means fabric formation direction. The FF direction runs parallel to the direction that the fabric is formed and leaves a knitting machine.
FW means fabric width direction. The FW direction runs perpendicular to the direction that the fabric is formed and leaves a knitting machine, i.e., the FW direction runs perpendicular to the FF direction.
16 N-FF means the test sample was aligned in the fixture in the FF direction with a 16 N load.
16 N-FW means the test sample was aligned in the fixture in the FW direction with a 16 N load.

By measuring elongation at both FF and FW directions, product anisotropy can be evaluated. The elongation properties as shown in Table 4 were achieved, in part, by creating a symmetrical, diamond shaped pore that allows for bidirectional stretch. Selected further physical properties of an embodiment of the device described herein are shown in Table 5.

TABLE 5

| Test Parameter | Mean value |
|---|---|
| Burst Strength (MPa) | 0.48[1] |
| Maximum Tensile Stress (MPa)-FF | 0.28[1] |
| Maximum Tensile Stress (MPa)-FW | 0.13 |
| % Elongation at break-FF | 112[1] |
| % elongation at break-FW | 103[1] |
| Tear Strength (N)-FF | 150.8[1] |
| Tear Strength (N)-FW | 81.5[1] |
| Suture Pull-Out force (N)/suture-FF | 15.5[1] |
| Suture Pull-Out force (N)/suture-FW | 19.1[1] |
| % Elongation at 16 N-FF | 31[1] |
| % Elongation at 16 N-FW | 39[1] |
| Density (mg/mm³) | 0.13[1] |

[1]n = 20 devices
[2]n = 15 devices
Table Legend
MPa means Mega Pascal
FF means fabric formation direction as described above
FW means fabric width direction as described above
N means Newton
mg/mm³ means milligram per cubic millimeter.

The average burst strength was determined by ball burst testing in accordance with ASTM D3787-07 as described above.

The average maximum tensile stress and elongation at break in the FF or FW direction were determined with a tensile testing in accordance with ASTM D5035, for example, using a sample size of about 60 mm in length and about 40 mm in width. It should be noted that a sample was cut from a silk fibroin mesh described herein according to whether the FF or FW direction was evaluated. For example, a sample was cut lengthwise along the FF direction for measurements of the average elongation at break along the FF direction. Similarly, a sample is cut lengthwise along the FW direction for measurements of the average elongation at break along the FW direction. The samples were incubated in phosphate buffered saline at 37° C. for about 2 hours before the testing.

In accordance with ASTM D5035, device samples were clamped in a mechanical test equipment. The upper clamp was mounted to a load cell, which was attached to the actuator and the lower clamp was mounted to a support plate. The lower limit of the actuator was set so that the upper and lower clamps were prevented from colliding. The upper clamp was aligned to make the faces of both clamps parallel to each other. The height of the mechanical equipment crosshead was adjusted so that the actuator was positioned to allow for a defined amount of upward movement and a specific sample gauge length resided between the upper and lower sample clamps.

For example, a sample (e.g., with a size of about 60 mm in length and about 40 mm in width) was loaded by clamping the first 10 mm of the sample into the upper clamp and allowing the remainder of the sample to fall unrestrained into the bottom clamp opening. The last 10 mm of the sample was held by the bottom clamp. Care was taken to avoid pre-straining the device sample. Once the sample was clamped the actuator height was adjusted so that the sample had a pre-load of 2N. The actuator position was adjusted to achieve a specific gauge length (e.g., 40 mm) and then reset to the zero-position at this point. The device sample was strained at an appropriate rate (e.g., about 1920 N/min) until it experienced ultimate tensile failure. The average maximum tensile stress and percent elongation at break were determined.

Maximum tensile stress was calculated using the equation:

$$\text{Maximum Tensile Stress}[MPa] = \left[\frac{\text{Maximim Tensile Strength}[N]}{\text{Width}[m] \times \text{Thickness}[m]}\right] \times 10^{-6}$$

where the thickness and width were provided by the respective device sample thickness and width measurements as determined after the sample was allowed to relax or equilibrate after completion of knitting.

Percent elongation at break was determined using the following equation:

$$PercentElongationBreak[\%] = \left[\frac{\text{Elongation at Break}[mm]}{\text{Length}[mm]}\right]\%$$

wherein, length is provided by the respective device sample length measurement as determined after the sample was allowed to relax or equilibrate after completion of knitting.

Average tear strength was determined by tear testing as described below. A device sample with a width that is two-thirds that of the length, for example, a sample size of about 60 mm in length and about 40 mm in width, was cut from each silk fibroin mesh described herein. It should be noted that a sample was cut from a silk fibroin mesh described herein according to whether the FF or FW direction was evaluated. For example, a sample was cut lengthwise along the FF direction for measurements of the average tear strength along the FF direction. Similarly, a sample is cut lengthwise along the FW direction for measurements of the average tear strength along the FW direction. Before the samples are incubated in phosphate buffered saline, a small cut that was one-fourth the size of the sample width was made in the center of the device sample perpendicular to the length (through a single row of wales). Mechanical test equipment was used to measure the maximum tear resistance load. Clamps were inserted in the equipment. The upper clamp was mounted to the load cell that was attached to the actuator and the lower clamp was mounted to the base support plate. The lower limit of the actuator was set so that the upper and lower clamps were prevented from colliding. The upper clamp was aligned to make the faces of both clamps parallel to each other. The height of the mechanical equipment crosshead was adjusted so that the actuator was positioned to allow for a defined amount of upward movement and a specific sample gauge length resided between the upper and lower clamps. The device sample was placed in the upper clamp. The top 10 mm of the sample was covered by the clamp. The device sample was positioned so that the cut was located on the left side. The sample was aligned perpendicular with the clamp before the clamp was closed. The bottom portion of the sample was allowed to fall unrestrained into the bottom clamp opening. The clamp was closed and the sample was preloaded with 1 N of force. The sample was strained at a constant rate (e.g., at a rate of about 2400 mm/min) until the sample tore at the cut point. From the resulting data the maximum tear resistance load was obtained.

Suture pull-out force per suture along the FF or FW direction was a measure of strength per suture of a sample device described herein. A device sample, for example, having a sample size of about 40 mm in length and about 20 mm in width, was cut from each silk fibroin mesh described herein. It should be noted that a sample was cut from a silk fibroin mesh described herein according to whether the FF or FW direction was evaluated. For example, a sample was cut lengthwise along the FF direction for measurements of the average suture pull-out force per suture along the FF direction. Similarly, a sample is cut lengthwise along the FW direction for measurements of the average suture pull-out force along the FW direction. The samples were incubated in phosphate buffered saline before testing. The sample device was placed over three suture anchors of a sawbone so that all three suture anchors align along the same horizontal row of pores of the sample device, e.g., about 3 mm or about 10 mm above the 20 mm sample edge. The sample device was then fastened to the sawbone with sutures using the following knotting arrangement: Surgeon's friction knot, square knot, square knot. The knots were looped diagonally over the intersection of one course and one wale. Mechanical test equipment was used to measure the maximum suture pull-out force. Clamps were inserted in the equipment. The upper clamp was mounted to the load cell that was attached to the actuator and the lower clamp was mounted to the base support plate. The sawbone was inserted into the lower clamp while the top 10 mm of the sample (the end that was opposing from the sawbone) was covered by the upper clamp. The sample was aligned perpendicular with the clamp before the clamp was closed. The clamp was closed and the sample was preloaded with about 1-2 N of force. The sample was strained at a constant rate (e.g., at a rate of about 1620 mm/min) until the suture was pulled out. From the resulting data, the maximum suture pull-out load was obtained. Since a three-anchor suture system was used, the average suture pull-force per suture can be determined by dividing the maximum suture pull-out load by three.

In this example, the sample device was characterized in that the suture pull-out force per suture (along the FF direction) was about 11 N/suture to about 20 N/suture or about 11 N/suture to about 16 N/suture, and the suture pull-out force per suture (along the FW direction) was about 11 N/suture to about 30 N/suture or about 15 N/suture to about 20 N/suture.

Example 2. Use of Pliable Silk Device in Two Stage Breast Reconstruction

The pliable silk device of Example 1 ("the device") can be used as a transitory scaffold for soft tissue support and repair in two-stage breast reconstruction to reinforce deficiencies where weakness or voids existed that required the addition of material to obtain the desired surgical outcome. The device is supplied sterile in a separate packaging with one device utilized per breast. The device placed during each subject's stage I breast reconstruction with a tissue expander placement procedure. Following mastectomy (either immediate or delayed), the surgical site is readied for subpectoral tissue expander insertion in accordance with standard surgical methods. The tissue expander is rinsed in antibiotic solution (according to standard of care) and inserted into the subpectoral pocket. The device is cut to size (prior to, during, and/or after suturing) to repair the void between the pectoral muscle and the chest wall (e.g., inframammary fold region). The device is rinsed with antibiotic solution and sutured in place, with a minimum suture bite of 3 mm or one full row of material. If any cutting is performed in situ, rinsing of the implant site is performed. Intra-operative photography is taken of the device prior to closure. The tissue expander is filled as appropriate, drains placed according to usual standard of care and number and location of drain(s) noted. Standard rinsing of the surgical site and closure is performed. Prophylactic antibiotic use and duration is documented.

In a second surgical procedure, the tissue expander is removed and replaced with a breast implant. The surgical approach used to remove the tissue expander. Implant placement is subpectoralis muscle and the pocket is prepared. The breast implant is rinsed in antibiotic solution and positioned within the pocket. Closure of the surgical site is performed.

The device provides soft tissue support and facilitates positioning of the implanted tissue expander. The stage I implanted expander is a temporary implant. The stage II breast implant is intended to be a permanent implant, typically remaining implanted in the patient for ten or more years. The device also provides stabilization of the pectoralis muscle and can as well assist with maintenance of the position and appearance of the inframammary fold during stage I of a breast reconstruction and can provide this function after stage I as well. At the time of stage II (when the tissue expander is removed and the breast implant is implanted) the device is then fully or at least partially integrated within the underlying soft tissue which has grown into and around the pores of the scaffold. The device begins to be bioresorbed as soon as the device had been implanted in a patient and the device is completely bioresorbed after about one to four years after implantation. The device is implanted at stage I to help hold the tissue expander in place (the device is sutured in to form a pocket in which the tissue expander rests and/or the device is draped over the tissue expander). At the time of stage II when the tissue expander is removed and replaced by a breast implant (saline or gel filled) the device is not removed and the device remains in place within the patient.

Preferably, no additional or further device is implanted in the patient at stage II or thereafter. Importantly, the device implanted in the patient in stage I provides soft tissue support and along with the implanted tissue expander maintains the existence of a pocket or space during stage I (the tissue expansion stage) that is until the stage II breast implant implantation in the patient into the pocket or space so maintained during stage I. Thus the device assists to ensure that a pocket or space is available for the placement of the stage II breast implant. Significantly, the stage I implanted device is left in place implanted in the patient and is not removed. By stage II the device has be incorporated into the underlying soft tissue and vasculature has grown in and around it.

Preferably the scaffold is comprised entirely of or consists essentially of sericin depleted, knitted silkworm silk. The implanted device begins to be biodegraded or bioresorbed as soon as it is implanted in a patient. The fabric is completely (100%) bioresorbed (biodegraded) within about one year to about four years after implantation in a patient.

Example 3. Use of Pliable Silk Device in Breast Tissue, e.g., Single Stage Breast Reconstruction The device of Example 1 is supplied sterile in a single-use size with one device utilized per breast. As an example, the device is implanted in a subject in need thereof immediately post mastectomy, during the breast implant placement surgery, in a direct-to-implant (DTI) breast reconstruction procedure. In this Example the device is used in DTI breast reconstruction.

Following mastectomy, the surgical site is readied for subpectoral breast implant insertion in accordance with standard surgical methods. The breast implant is rinsed in antibiotic solution and inserted into the subpectoral pocket. The device is optionally cut to size (prior to, during, and/or after suturing) to repair the void between the pectoral muscle and the chest wall (e.g., inframammary fold region). The device is rinsed with antibiotic solution and sutured in place to both the pectoralis muscle and chest wall, with a minimum suture bite of 3 mm or one full row of material. If any cutting was performed in situ, rinsing of the implant site is performed. Drains are placed according to usual standard of care and number and location of drain(s) noted. Rinsing of the surgical site with antibiotic solution and closure is performed. The surgical drain(s) is removed when deemed appropriate. The result is that the patient has breasts properly positioned and proportioned which look and feel like normal breasts. The same or a very similar procedure can be used for breast augmentation using the device.

Other exemplary single-stage breast reconstruction procedures include, but are not limited to mastopexy surgery, breast revision surgery, and intra-mammary fold surgery. Thus, in some embodiments, the devices described herein can be used for various breast-related supporting and/or contouring procedures, including, e.g., but not limited to mastopexy, breast revision surgery, intra-mammary fold surgery, and the like. In addition, the devices described herein are suitable for supporting and "lifting" the breast implant, or provide reinforcement to soft tissue surrounding the implant during and after these procedures.

Example 4. General Surgical Procedures for Use of the Device

The device can be used as a transitory scaffold for soft tissue support and repair to reinforce deficiencies where weakness or voids exist that require the addition of material to obtain the desired surgical outcome, including but not limited to reinforcement of soft tissues in reconstructive and plastic surgery to obtain the desired aesthetic outcome. The device should not be used in patients with a known allergy to silk.

Handling and Using the Device:
1. Irrigate and aspirate the device implant site with saline following the in situ cutting of the device to remove any device particulate debris that may have been generated.
2. Store the device in its original sealed package away from direct sources of heat at ambient room temperature.
3. Handle the device using aseptic technique and sterile talc-free gloves.
4. Remove the device from the package. Although the device does not require rehydration for mechanical or physical performance, a brief incubation (minimum 2-3 seconds) in sterile rinse solution is recommended prior to implantation.
5. Use the type of suture or fixation system that is appropriate for the patient use.
6. Sutures should be placed at least 3 mm, or one full row, from the cut edge of the device.
7. If preferred, the uncut device can be sutured over the patient defect and trimmed once secured in place followed by rinsing and aspiration.
8. The device should be sufficiently anchored to stabilize it during tissue ingrowth.
9. For laparoscopic procedures, the device should be rolled along its long axis and may be delivered through a ⅞ mm or larger cannula.

Example 5. Use of Pliable Silk Device for Hernia Repair

In some embodiments, the devices described herein can be applied to different tissues in hernia procedures including, e.g., but not limited to umbilical, ventral wall, inguinal, hiatal, femoral, paraesophageal, flank, and the like.

In general, there are two main types of hernia repair: open hernia repair and minimally invasive (laparoscopic) repair. Open repair is a traditional hernia repair procedure. There are numerous and varied approaches for performing this type of hernia repair. Such approaches are performed routinely with local and intravenous sedation. Due to the larger size of the incision, open hernia repair is generally painful with a relatively long recovery period. Minimally invasive (laparoscopic) repair is usually performed under general anesthesia. Spinal anesthesia and local anesthesia are used under certain circumstances. Benefits associated with minimally invasive (laparoscopic) repair include shorter operative time, less pain, and a shorter recovery period.

In laparoscopic hernia surgery, a telescope attached to a camera is inserted through a small incision that is made under the patient's belly button. Two other small cuts are made in the lower abdomen. The hernia defect is reinforced with a mesh and secured in position. The device is secured in position by stitches, staples, tacks, and glue.

Another form of laparoscopic hernia repair is ventral hernia repair (laparoscopic). Incisional, ventral, epigastric, or umbilical hernias are defects of the anterior abdominal wall and may be congenital (umbilical hernia) or acquired (incisional). Incisional hernias form after surgery through the incision site or previous drain sites, or laparoscopic trocar insertion sites. Incisional hernias often occur after open surgical procedures. These hernias present with a bulge near or at a previous incision. The device (a prosthetic mesh) is used in order to minimize tension on the repair so as to reduce the chance of hernia recurrence. Traditionally, an old incision scar is incised and removed. Inspection of the entire length of the incision generally uncovers multiple hernia defects. The area requiring coverage is usually large and requires much surgical dissection. The device is used to cover the defect before closure of the wound. This is a major and often complex surgical procedure. The use of the device decreases possible recurrence. A patient typically returns to normal activity within a matter of weeks. The principles governing a laparoscopic ventral hernia repair are based on those of open Stoppa ventral hernia repair. A large piece of the device is placed under the hernia defect with a wide margin of mesh outside the defect, and the mesh is anchored in to place and secured to the anterior abdominal wall. The device is anchored into place, for example, by sutures. The device is secured to the anterior abdominal wall, for example, by tacks which are placed laparoscopically.

Example 6. Use of the Device in Body Aesthetics and/or Body Contouring Procedures The device can be used in body aesthetics and body contouring surgical procedures, including, e.g., but not limited to tummy tucks, umbilical hernia, brachyoplasty, abdominoplasty, and the like.

One such embodiment relates to use of the device in abdominoplasty. There are various surgical procedures for performing an abdominoplasty depending upon the type of abdominoplasty to be performed. The time needed for conducting an abdominoplasty also varies depending upon the type of abdominoplasty to be performed. For example, a complete abdominoplasty typically is completed in 1 to 5 hours. A partial abdominoplasty, also referred to as a mini-tuck abdominoplasty, is typically completed in 1 to 2 hours. Following an abdominoplasty surgical procedure, reconstruction of the umbilicus, commonly referred to as the belly button, may also occur. The original umbilicus is attached, such as by sutures, into a new hole created by the surgeon.

A complete abdominoplasty is also referred to as a full abdominoplasty. In a complete abdominoplasty, an incision is made from hip to hip just above the pubic area. Another incision is made to separate the navel from the surrounding skin. The skin is detached from the abdominal wall to reveal the muscles and fascia to be tightened. The muscle fascia wall is tightened with sutures. The remaining skin and fat are tightened by removing the excess and closing. The old belly button stalk is brought out through a new hole and sutured into place. Liposuction may also be used to refine the transition zones of the abdominal contouring. A surgical dressing and optionally a compression garment are applied. Excess fluid from the site is drained. A complete abdominoplasty may also comprise a musculofascial plication abdominal dermal lipectomy and/or suction-assisted lipectomy of hips.

A partial abdominoplasty is also referred to as a mini-abdominoplasty. In a partial abdominoplasty, a smaller incision is made as compared to a complete abdominoplasty. The skin and fat of the lower abdomen are detached in a more limited manner from the muscle fascia. The skin is stretched down and excess skin removed. The belly button stalk may be divided from the muscle below and the belly button slid down lower on the abdominal wall.

A portion of the abdominal muscle fascia wall is optionally tightened. Liposuction may be used to contour or sculpt the transition zone. The flap is stitched back into place. A combination abdominoplasty and liposuction procedure is often referred to as a "lipo-tuck". During such procedure, skin is removed and subsequently sutured. As noted above, the belly button is reattached to a new hole created by the surgeon.

An extended abdominoplasty is a complete abdominoplasty plus a lateral thigh lift. The patient is cut from the posterior axillary line. The operation includes all of the abdominal contouring of a complete abdominoplasty plus allows further improvement of the flank (waist), as well as smoothing the contour of the upper lateral thigh.

A high lateral tension tummy tuck is a more involved procedure and typically takes at least four and half hours to perform. In this method, in addition to vertical-line tightening as is the case in most conventional abdominoplasty procedures, muscles are also tightened horizontally. The procedure provides a patient with a flat abdomen and with an improved waistline.

A circumferential abdominoplasty, also referred to as a belt lipectomy or body lift, is an extended abdominoplasty in conjunction with a buttock lift. The incision typically runs all the way around the body. This surgical procedure is suitable, for example, for patients who have undergone massive weight loss.

The above procedures can be used alone or in combination. For example, an abdominoplasty may be conducted in the course of a lower body lift. Alternatively, abdominoplasty is combinable with liposuction contouring, breast reduction, breast lift, or a hysterectomy. Breast enhancement procedures performed in conjunction with an abdominoplasty are often referred to as a "mommy makeover". In such a procedure, barbed sutures may be employed.

An abdominoplasty procedure can be conducted using a device of the present invention. For example, a typical fascial is done first, using a row of figure of eight sutures, first and then another layer of running suture all #1 PDS (polydioxanone suture, Ethicon). Two pieces of the device can be used as an onlay to augment the fascia tightening. One 10×25 cm piece of the device can be used in the lower abdomen. It can be laced transversely, the vertical dimension 10 cm, can be positioned with the lower edge at level of the pubic symphysis, and the upper edge at the lower border of the umbilicus. The 25 cm transverse dimension can be suitable. A second scaffold can be cut and tailored to use in the supra-umbilical region, with care taken not to leave too close to the umbilical closure. As the closure around the umbilicus occasionally may not heal primarily, extra care is taken with sutures/device in this location.

The device may be secured at its periphery with a 3-0 V-Lock (COVIDIEN brand of barbed suture, made of a material similar to PDS).

The patient may be hospitalized overnight. The patient may have a total of 5 10 mm flat Blake drains, for example, two drains that drain in the back and three drains that drain in the front. The patient may be treated with antibiotics until draining is complete, or s typically within 10 to 20 days.

Example 7. Use of the Device in Facial Area and Other Applications

The device can be used in a facial area, e.g., for face lift, nasal septum reconstruction or for general soft tissue reinforcement in areas such as the back of the mouth. In face lift procedures, for example, one or more strips of an exemplary device described herein can be implanted under a facial skin and stitched in an area between the temple and below the chin of a subject in need thereof and then pulled tight to give the appearance of tightened facial skin, and reduced wrinkles.

Other applications include placing them on a skin as a way to protect wounds and/or recruit cells/build connective tissue in the face or body. Examples of such applications can be used for oncology lesions (e.g., in the cheek and nose), or wounds on the face (e.g., if the wound is too large to be closed by suture).

To summarize, one embodiment presented herein is a biocompatible, bioresorbable, pliable surgical matrix (mesh or scaffold) made preferably from the silk fibroin of the *Bombyx mori* silkworm. Because raw silk fibers are comprised of a fibroin protein core filament that is naturally coated with the antigenic globular protein sericin the sericin is removed by aqueous extraction. Yarn is then made from the sericin-depleted fibroin protein filaments by helical twisting to form a multi-filament protein fiber. The multi-filament protein fiber yarn is then knit into a three dimensional patterned matrix (mesh or scaffold) that can be used for soft tissue support and repair. The device upon implantation provides immediate physical and mechanical stabilization of tissue defects because of its strength and porous construction. Additionally, the porous lattice design of the device facilitates native tissue generation (that is tissue ingrowth) and neovascularization. The natural tissue repair process begins with deposition of a collagen network. This network integrates within the protein matrix, interweaving with the porous construct. Neovascularization begins with endothelial cell migration and blood vessel formation in the developing functional tissue network. This new functional tissue network and its corresponding vascular bed ensure the structural integrity and strength of the tissue. In the beginning stages of the tissue ingrowth process, the device provides the majority of structural support. The device is gradually deconstructed (bioresorbed) into its amino acid building blocks. The slow progression of the natural biological process of bioresorption allows for the gradual transition of support from the protein matrix of the device to the healthy native tissue thereby achieving the desired surgical outcome.

While this invention has been described with respect to various specific examples and embodiments, it is to be understood that the invention is not limited thereto and that it can be variously practiced within the scope of the invention.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

"About" means plus or minus ten percent or lower (e.g., 10%, 9%, 8%, 7%, 6%, 5%, 4%, 3%, 2%, or 1%) of the quantity, number, range or parameter so qualified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A process for forming a pliable silk fibroin mesh, the process comprising the steps of:
   knitting a first silk fibroin yarn in a first wale direction using the knit pattern 1/1-1/3-3/3-3/1;
   knitting a second silk fibroin yarn in a second wale direction using the knit pattern 3/1-1/1-1/3-3/3;
   knitting a third silk fibroin yarn in a first course direction using the knit pattern 1/1-5/5-5/5-3/3-3/3-5/5-5/5-3/3-3/3-7/7-7/7-3/3-3/3-5/5-5/5-3/3-3/3-5/5-5/5-3/3-3/3-5/5-5/5-3/3-3/3-5/5-5/5-3/3; and
   knitting a fourth silk fibroin yarn in a second course direction using the knit pattern 3/3-3/3-5/5-5/5-3/3-3/3-5/5-5/5-1/1-1/1-5/5-5/5-3/3-3/3-5/5-5/5-3/3-3/3-7/7-7/7-3/3-3/3-5/5-5/5-3/3-3/3-5/5-5/5,
   thereby forming the pliable silk fibroin mesh.

2. The process of claim 1, wherein the pliable silk fibroin mesh is characterized in that elongation at break along a direction of the pliable silk fibroin mesh formation is greater than 85% and elongation at break along a width of the pliable silk fibroin mesh is greater than 85%.

3. The process of claim 1, wherein the pliable silk fibroin mesh comprises pores having an average pore area of greater than 1 mm$^2$.

4. The process of claim 1, wherein the silk fibroin yarn comprises silk fibroin fibers.

5. The process of claim 1, wherein the silk fibroin yarn is sericin-depleted.

6. A pliable silk fibroin mesh formed by a process comprising:
   knitting a first silk fibroin yarn in a first wale direction using the knit pattern 3/1-1/1-1/3-3/3;
   knitting a second silk fibroin yarn in a second wale direction using the knit pattern 1/1-1/3-3/3-3/1;
   knitting a third silk fibroin yarn in a first course direction using the knit pattern 3/3-3/3-5/5-5/5-3/3-3/3-5/5-5/5-1/1-1/1-5/5-5/5-3/3-3/3-5/5-5/5-3/3-3/3-7/7-7/7-3/3-3/3-5/5-5/5-3/3-3/3-5/5-5/5; and
   knitting a fourth silk fibroin yarn in a second course direction using the knit pattern 1/1-5/5-5/5-3/3-3/3-5/5-5/5-3/3-3/3-7/7-7/7-3/3-3/3-5/5-5/5-3/3-3/3-5/5-5/5-3/3-3/3-5/5-5/5-3/3-3/3-5/5-5/5-3/3.

7. The pliable silk fibroin mesh of claim 6, wherein the pliable silk fibroin mesh is characterized in that elongation at break along a direction of the pliable silk fibroin mesh formation is greater than 85% and elongation at break along a width of the pliable silk fibroin mesh is greater than 85%.

8. The pliable silk fibroin mesh of claim 6, wherein the pliable silk fibroin mesh comprises pores having an average pore area of greater than 1 mm$^2$.

9. The pliable silk fibroin mesh of claim 6, wherein the silk fibroin yarns are made of nine filament and twisted silk fibroin fibers.

10. The pliable silk fibroin mesh of claim 6, wherein the silk fibroin yarn is sericin-depleted.

11. An implantable device comprising a knitted network of silk fibroin yarns, wherein the knitted network is characterized in that average elongation at break along a direction of the knitted network formation is greater than 85% and average elongation at break along a width of the knitted network is greater than 85%, and wherein the average pore size of the knitted network is greater than 1 mm$^2$.

12. The implantable device of claim 11, wherein the knitted network exhibits one or more of the following characteristics:
   (a) an average burst strength of about 0.3 MPa to about 1.5 MPa, or about 0.3 MPa to about 0.6 MPa;
   (b) an average maximum tensile stress along the direction of the knitted network formation of about 0.2 MPa to about 0.4 MPa, or about 0.2 MPa to about 0.3 MPa;
   (c) an average maximum tensile stress along the width of the knitted network of about 0.1 MPa to about 0.3 MPa, or about 0.15 MPa to about 0.2 MPa;
   (d) an average tear strength along the direction of the knitted network formation of about 100 N to about 170 N or about 110 N to about 160 N;
   (e) an average tear strength along the width of the knitted network of about 50 N to about 100 N or about 60 N to about 90 N;
   (f) an average density of about 0.10 mg/mm$^3$ to about 0.15 mg/mm$^3$;
   (g) an average elongation at a force of about 16 N along the direction of the knitted network formation of about 20% to about 50% or about 25% to about 40%; and
   (h) an average elongation at a force of about 16 N along the width of the knitted network formation of about 20% to about 60% or about 30% to about 50%.

13. The implantable device of claim 11, wherein the silk fibroin yarn comprises silk fibroin fibers.

14. The implantable device of claim 11, wherein the silk fibroin yarn is sericin-depleted.

15. The implantable device of claim 11, wherein the silk fibroin yarn is made of 9 silk fibroin fibers.

16. The implantable device of claim 11, wherein the knitted network is formed by a process comprising at least one of the following steps:
   (i) knitting a first silk fibroin yarn in a first wale direction using a knit pattern 1/1-1/3-3/3-3/1 or a portion thereof;
   (ii) knitting a second silk fibroin yarn in a second wale direction using a knit pattern 3/1-1/1-1/3-3/3 or a portion thereof;
   (iii) knitting a third silk fibroin yarn in a first course direction using a knit pattern 1/1-5/5-5/5-3/3-3/3-5/5-5/5-3/3-3/3-7/7-7/7-3/3-3/3-5/5-5/5-3/3-3/3-5/5-5/5-3/3-3/3-5/5-5/5-3/3-3/3-5/5-5/5-3/3 or a portion thereof; and (iv) knitting a fourth silk fibroin yarn in a second course direction using a knit pattern 3/3-3/3-5/5-5/5-3/3-3/3-5/5-5/5-1/1-1/1-5/5-5/5-3/3-3/3-5/5-5/5-3/3-3/3-7/7-7/7-3/3-3/3-5/5-5/5-3/3-3/3-5/5-5/5 or a portion thereof.

17. The implantable device of claim 11, wherein the knitted network is formed by a process comprising at least one of the following steps:
  (i) knitting a first silk fibroin yarn in a first wale direction using a knit pattern 3/1-1/1-1/3-3/3 or a portion thereof;
  (ii) knitting a second silk fibroin yarn in a second wale direction using a knit pattern 1/1-1/3-3/3-3/1 or a portion thereof;
  (iii) knitting a third silk fibroin yarn in a first course direction using a knit pattern 3/3-3/3-5/5-5/5-3/3-3/3-5/5-5/5-1/1-1/1-5/5-5/5-3/3-3/3-5/5-5/5-3/3-3/3-7/7-7/7-3/3-3/3-5/5-5/5-3/3-3/3-5/5-5/5 or a portion thereof; and
  (iv) knitting a fourth silk fibroin yarn in a second course direction using the knit pattern 1/1-5/5-5/5-3/3-3/3-5/5-5/5-3/3-3/3-7/7-7/7-3/3-3/3-5/5-5/5-3/3-3/3-5/5-5/5-3/3-3/3-5/5-5/5-3/3-3/3-5/5-5/5-3/3 or a portion thereof.

* * * * *